United States Patent [19]
Ferres et al.

[11] 3,935,192
[45] Jan. 27, 1976

[54] PENICILLINS

[75] Inventors: Harry Ferres, Horsham; Adrian Victor Kemmenoe, Westcott; Desmond John Best, Sutton, all of England

[73] Assignee: Beecham Group Limited, Great Britain

[22] Filed: May 16, 1975

[21] Appl. No.: 578,262

Related U.S. Application Data

[62] Division of Ser. No. 466,814, May 3, 1974.

[30] Foreign Application Priority Data

May 4, 1973 United Kingdom............... 21203/73

[52] U.S. Cl. .............................................. 260/239.1
[51] Int. Cl.² ...................................... C07D 449/44
[58] Field of Search .................................. 260/239.1

[56] References Cited

UNITED STATES PATENTS

| | | | |
|---|---|---|---|
| 3,340,252 | 9/1957 | Alburn et al...................... | 260/239.1 |
| 3,483,188 | 12/1969 | McGregor......................... | 260/239.1 |

*Primary Examiner*—Gerald A. Schwartz

[57] ABSTRACT

New penicillins and their salts and esters particularly active against Gram-negative organisms such as Pseudomonas spp., and their preparation and administration. The penicillins are active against clinically important organisms against which well-known broad spectrum penicillins are inactive and may generally be designated as aminoacyldipeptide penicillins of unusual structure and properties.

8 Claims, No Drawings

PENICILLINS

CROSS-REFERENCE

This is a division of Ser. No. 466,814 filed May 3, 1974.

This invention relates to penicillins which have, in general, a broad spectrum of antibacterial activity, being active against many species of Gram-positive and Gram-negative bacteria. They are thus useful as therapeutic (and, to a lesser extent, prophylactic) agents in animals, including man and poultry. The invention further relates to methods for the preparation of these penicillins and to their use in therapy.

Although there are now available a number of semi-synthetic penicillins having what is known as broad-spectrum activity, no single penicillin is yet available which has a clinically useful level of antibacterial activity against all the pathogenic organisms encountered in clinical practice. The search thus continues for broad-spectrum penicillins which have advantages, either in improved antibacterial effectiveness or wider spectrum of activity, over the available penicillins.

According to the present invention there is provided a penicillin of formula (I) or a pharmaceutically acceptable salt or ester thereof:

$$R-CH-CO-NH$$
$$|$$
$$NH$$
$$|$$
$$CO$$
$$|$$
$$R^1-CH_2-C-R^2$$
$$|$$
$$R^3$$

(I)

wherein
R is phenyl, phenyl substituted by one or more functional groups selected from hydroxy, halogen, nitro, alkoxy containing from 1 to 3 carbon atoms, and amino groups, 2- or 3- thienyl, cycloalkyl having from 3 to 7 carbon atoms, cycloalkenyl having from 5 to 7 carbon atoms or alkyl having from 1 to 4 carbon atoms;

$R^3$ is hydrogen or an alkyl group having from 1 to 3 carbon atoms;

$R^1$ is hydrogen or an organic radical containing up to 20 carbon atoms;

$R^2$ is a group of formula (II) or (III):

$$\begin{array}{cc} -NH & -NH \\ | & | \\ C-R^5 \quad (II) & C-R^6 \quad (III) \\ \| & \| \\ O & NH \end{array}$$

wherein $R^5$ is amino, mono- or di-alkylamino wherein the alkyl groups contain from 1 to 4 carbon atoms, cyclohexylamino, hydrogen, alkyl having from 1 to 4 carbon atoms, or phenyl and $R^6$ is amino or mono- or di- alkylamino wherein the alkyl groups contain from 1 to 4 carbon atoms, or cyclohexylamino.

The group R may be, for example, phenyl, 4-hydroxyphenyl, 3-chloro-4-hydroxyphenyl, 4-nitrophenyl, 4-chlorophenyl, 4-fluorophenyl, 4-methoxy-phenyl, 4-aminophenyl, 2-thienyl, 3-thienyl, cyclopropyl, cyclohexyl, cyclohexa-1,4-dienyl, iso-propyl or methyl.

The group $R^1$ may, for example, be hydrogen, phenyl, 4-hydroxyphenyl, 4-nitrophenyl, 4-chlorophenyl, 4-fluorophenyl, 4-methoxyphenyl, 4-aminophenyl, methyl, ethyl, n-propyl, isopropyl, n-butyl, isobutyl, tertbutyl, methoxy, ethoxy, n-propoxy, isopropoxy, methylene, ethylene, ethylthio, n-propoxy-methyl, carbamyl, carbamylmethyl, acetoxy, phenoxy, benzyloxy, 2-thienyl, 3-thienyl, indol-3-yl, 1H-imidazol-5-yl, cyclohexa-1,4-dienyl, cyclopropyl or cyclohexyl.

The group $R^5$ may, for example, be amino, methylamino, n-butylamino, tert-butylamino, cyclohexylamino, hydrogen, methyl, ethyl, n- or isopropyl, n-, sec, or tert-butyl, or phenyl.

The group $R^6$ may, for example, be amino, methylamino, dimethylamino, ethylamino, diethylamino, n-propylamino, isopropylamino, tert-butylamino, n-butylamino or cyclohexylamino.

Preferably R is phenyl, 4-hydroxyphenyl, or 3-thienyl.

Preferably $R^1$ is phenyl, 4-hydroxyphenyl, 4-chlorophenyl, 4-fluorophenyl, 4-nitrophenyl, 3-indolyl, or methylthiomethyl.

Preferably $R^3$ is hydrogen.

Preferably $R^5$ is amino or hydrogen.

Preferably $R^6$ is amino.

Preferably the carbon atom to which the group R in formula (I) is attached is in the D configuration.

Preferably the carbon atom to which the group $R^2$ in formula (I) is attached is in the D configuration.

Examples of suitable salts of compounds (I) include the sodium, potassium, calcium, magnesium or aluminium salts, and ammonium or substituted ammonium salts, for example those with trialkylamines such as triethylamine, procaine, dibenzylamine, triethanolamine, 1-ephenamine, ethylpiperidine, and other amines which have been used to form salts with benzylpenicillins. In the case of compounds (I) which contain a basic nitrogen site in the side chain, acid addition salts may also be formed. Such salts include, for example, inorganic salts such as the sulphate, nitrate, phosphate, borate, thiocyanate, and hydrohalides, e.g. hydrochloride, hydrobromide and hydroiodide, and organic salts such as the acetate, oxalate, tartrate, malate, citrate, succinate, benzoate, ascorbate and methanesulphonate.

Examples of suitable pharmaceutically acceptable esters include those which break down readily in the human body to leave the parent acid, e.g., acyloxyalkyl esters such as acetoxymethyl, pivaloyloxymethyl, $\alpha$-acetoxyethyl, $\alpha$-acetoxybenzyl and $\alpha$-pivaloyloxymethyl esters, and alkoxycarbonylalkyl esters such as methoxy carbonyloxymethyl esters. Other suitable esters of this readily hydrolysable type include lactone, thiolactone, and dithiolactone esters (i.e. compounds of formula (I) wherein the 3-carboxy group is esterified to produce a grouping of formula:

$$-CO-O-CH-Z^1$$
$$|\quad |$$
$$X^1-C=Y^1$$

wherein $X^1$ and $Y^1$ are oxygen or sulphur and $Z^1$ is a divalent hydrocarbon group), especially the phthalidyl and substituted phthalidyl esters e.g. 5,6-dimethoxyphthalidyl ester.

The compounds of this invention may be prepared by reacting 6-aminopenicillanic acid or a salt, ester or silyl derivative thereof with an N-acylating derivative of an acid of formula (IV)

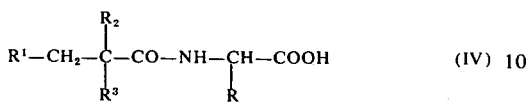  (IV)

in which any reactive substituents may be blocked, wherein R, R¹, R² and R³, are as defined in formula (I) and then, if necessary, carrying out one or more of the following steps (i) removing any silyl groups by hydrolysis or alcoholysis, (ii) converting an ester compound to a free acid or salt (iii) converting a salt to a free acid or a free acid to a salt (iv) removing any blocking groups to release the desired functional substituent (v) converting a free acid compound to an ester compound.

By the term "silyl derivative" used in connection with 6-aminopenicillanic acid (6-APA) we mean the product of the reaction between 6-APA and a silylating agent such as a halotrialkylsilane, halodialkylsilane, a halotrialkoxysilane, a dihalodialkoxysilane or a corresponding aryl or aralkyl silane and compounds such as hexamethyldisilazane. In general, halotrialkylsilanes are preferred, especially trimethylchorosilane.

A reactive N-acylating derivative of the acid (IV) is employed in the above process. The choice of reactive derivative will of course of influenced by the chemical nature of the substituents in the acid. Thus, when the acid contains only acid stable groups, an acid halide is a suitable N-acylating derivative, preferably the acid chloride.

Such reagents would, however, be avoided when an acid labile group was present in the acid (IV). In such cases a suitable N-acylating derivative is a mixed anhydride. For this purpose particularly convenient mixed anhydrides are the alkoxyformic anhydrides.

However, with both the acid chloride and mixed anhydride N-acylating agents we have found that some racemisation may take place. To minimise such unwanted racemisation, we prefer to use an activated ester as the N-acylating agent. Such activated esters, for example the ester formed with 1-hydroxybenzotriazole or, preferably, N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (II) include the reactive intermediate formed by reaction in situ with a carbodiimide or carbonyldiimidazole, but the literature on the preparation of semisynthetic penicillins contains examples of other reactive N-acylating derivatives of acids suitable for coupling to 6-APA.

It will be understood, of course, that where a free acid of type (I) or a salt thereof is desired, it may be convenient to carry out the acylation reaction using an ester of 6-APA, and then to remove the ester group. Vice versa, if an ester is required, it may be convenient to carry out the acylation reaction using 6-APA or a salt thereof and thereafter to esterify the free acid.

In the above process, if it is necessary to block any reactive substituents in the acid (IV), conventional chemical blocking groups are known. Thus, if desired, any free amino groups may be blocked by conversion to benzyloxycarbonylamino groups, or the amino group may be blocked as the nitro group which is later converted to the amino group.

The compounds of this invention may also be prepared by a process which comprises reacting a compound of formula (V) or a salt, ester or silyl derivative thereof.

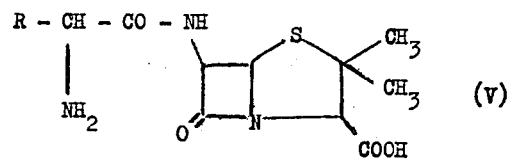

wherein R is as defined in formula (I) and in which any reactive substituents may be blocked, with an N-acylating derivative of an acid of formula (VI)

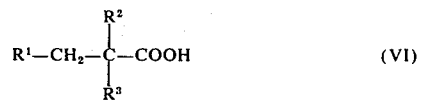  (VI)

wherein R¹, R² and R³ are as defined in formula (I), and if necessary, carrying out one or more of the following steps (i) removing any silyl groups by hydrolysis or alcoholysis, (ii) converting an ester compound to a free acid or salt thereof (iii) converting a salt to a free acid or a free acid to a salt (iv) removing any blocking groups to release the desired functional substituents (v) converting a free acid compound to an ester compound.

The remarks made earlier with respect to silyl derivatives, N-acylating derivatives, and blocking groups, also apply to this process.

The compounds of this invention wherein R¹ is a group of formula (II) may also be prepared by reacting a compound of formula (VII) or a salt, ester or silyl derivative thereof:

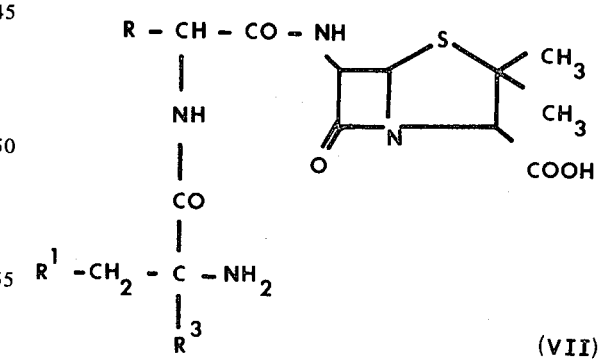

wherein R, R¹, R³ and R⁴ are as defined in formula (I) and wherein any reactive substituents may be blocked, with cyanate ion, a $C_{1-4}$ alkyl isocyanate, cyclohexyl isocyanate, a formylating agent or an N-acylating derivative of an acid R⁶COOH wherein R⁶ is phenyl or an alkyl group having from 1 to 4 carbon atoms, followed, if necessary, by one or more of the following steps (i) removing any silyl groups by alcoholysis or hydrolysis, (ii) converting an ester compound to a free acid or salt thereof, (iii) converting a salt to a free acid or a free acid to a salt (iv) removing any blocking groups to release the desired functional substituent, (v) converting a free acid compound to an ester compound.

It will be noted that the above process essentially consists in generating the desired group $R^2$ from the free amino group in compound (VII). The reaction of amino compounds with cyanate ion and isocyanates to produce ureas and substituted ureas is well known. Likewise the formylation of amino compounds (e.g., using formic acid and acetic anhydride) is well known. Similarly, the acylation of amino compounds is extremely well known, and suitable N-acylating derivatives of acids have been discussed hereinbefore.

The compounds of this invention are broad spectrum penicillins, i.e. penicillins which not only have activity against Gram-positive bacteria, but also against a number of clinically important Gram-negative organisms. The preferred compounds of this invention are active against such important organisms as Pseudomonas spp. against which the most well known broad-spectrum penicillin (6[(D)α-aminophenylacetamido]penicillanic acid ... ampicillin) is normally inactive. Moreover the preferred compounds of this invention are about as active as 6[(D)α-carboxy-3-thienylacetamido] penicillanic acid against Pseudomonas spp., this latter compound being the most active of the known penicillins against those organisms. Several of the preferred compounds of this invention have minimum inhibitory concentrations of from 5 – 12.5 μg/ml against some β-lactamase producing strains of staphylococci, against which the majority of known broad spectrum penicillins are only marginally effective. The preferred compounds of this invention are not greatly serum-bound, and are not markedly inactivated by serum.

The penicillins of this invention show the characteristic lack of toxicity of penicillins generally. They may be administered by parenteral injection. The daily dose will depend on the identity of the pencillin and severity of infection. With the preferred compounds of this invention, a suitable average daily dose for an adult would be in the range of 100mg to 5000mg. An average single dose for an adult would be from 20 mg to 500 mg.

The following Examples illustrate the preparation of some of the compounds of this invention:

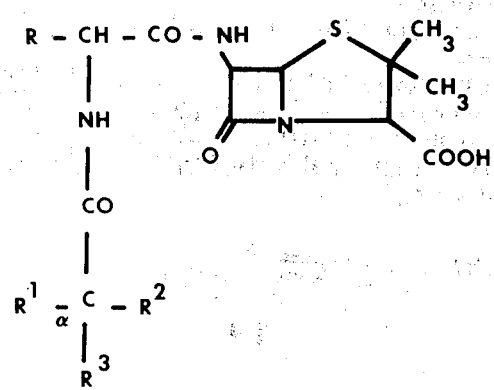

In the following Examples amoxycillin is the approved name for 6[D-α-amino-p-hydroxy-phenylacetamido]penicillanic acid and ampicillin is the approved name for 6[D-α-aminophenylacetamido] penicillanic acid. Epicillin is the approved name for [D-α-amino -cyclohexa-1,4,-dienylacetamido]penicillanic acid. All temperatures are in °C. All biochromatograms were run in butanol/ethanol/water. All compounds were made by one of the following generally applicable methods.

The majority of the starting materials used in the following Examples are known. However, the following literature references describe generally applicable methods which may be used to prepare the starting materials:

UREIDO-ACIDS

DAKIN: Amer.Chem. J. 44 54
ANDREASCH: Monats. 23. 805
NEVILLE, M$^c$GEE: Can.J.Chem. 41, 2123-9 (1963)
WIELAND: Bio.Z. 38, 389, Ann.3.
DAVIS, BLANCHARD: J.Amer.Chem.Soc. 51, 1797
LEUTHARDT, BRUNNER: Helv.Chim.Acta. 30, 964-5 (1947)

SUBSTITUTED UREIDO-ACIDS

BALL, SKINNER, SHIVE: Texas Rept. Biol.Med. 21(2) 188-75 (1963)
BRITISH PATENTS 1301961/2.

GUANIDINO-ACIDS

KAPFHAMMER, MILLER: Z. Physiol,Chem. 225, 1-12, (1934)
RADKA PANT: Ibid 335, 272-4 (1964)
FRAMM, KAPELLER: Ann. (1925) 442, 144
HABEL: Can.J.Biochem. Physiol. 38, 493 (1960)
RAMSAY: Ber. 41, 4390

FORMAMIDO-ACIDS

SHEEHAN, YOUNG: J.Amer.Chem.Soc. (1958), 80, 1154 ,110

METHOD A

A solution of the guanidino-acid, hydrochloride (5m. mole) in dry dimethylformamide (5 ml) was added over 10 mins. to a stirred solution of phthalid-3-yl D-α-aminophenyl-acetamidopenicillanate (5 m. mole) and N,N$^1$-dicyclohexylcarbodi-imide (5.8 m. mole) at 0°C in dry methylene dichloride.

After stirring at 0°C for 30 mins. and 1½ hours at ambient temperatures, the mixture was cooled to –10°C and the dicyclohexylurea removed by filtration.

The solution was washed with dilute hydrochloric acid (pH 1.5), water, and brine and the dried solution concentrated to low volume in vacuo to induce crystallisation. The filtered solid was dried under vacuum over phosphorus pentoxide.

METHOD B

Ureido- (or substituted-ureido-) acid (0.01 mole) in dry acetone (60 ml) at –10°C was treated with triethylamine (ca. 0.015 mole) and iso-butylchloroformate (0.01 mole) and stirred at –10°C for not more than 30 mins. D-α-aminophenylacetamidopenicillanic acid, trihydrate (0.01 mole) in water (60 ml) was treated with triethylamine to give a clear solution (pH 8.4). Acetone (60 ml) was added and the solution cooled to 0°C.

The mixed anhydride solution cooled to –40°C was filtered through Celite into the stirred penicillin solution and the mixture allowed to warm slowly to room temperature over 20 mins.

The acetone was evaporated in vacuo and the aqueous residue washed well with ether and then acidified to pH2 under a layer of ethyl acetate with 5N hydrochloric acid.

The product was obtained either as the free acid by filtration of the aqueous/ethyl acetate mixture or by precipitation from the ethyl acetate solution with potassium or sodium 2-ethylhexoate to give the corresponding alkali-metal salt.

Method Bi. As B, but using N-methylmorpholine instead of triethylamine in the preparation of the mixed anhydride.

Method Bii. As B, but using D-α-amino(p-hydroxyphenyl)acetamidopenicillanic acid, trihydrate instead of D-α-aminophenylacetamidopenicillanic acid, trihydrate.

Method Biii. As (Bii) but using N-methylmorpholine instead of triethylamine in the preparation of the mixed anhydride.

Method Biv. As (Bi), but using D-α-amino-(3-thienyl)-acetamidopenicillanic acid instead of D-α-aminophenylacetamidopenicillanic acid, trihydrate.

Method Bv. As (Bi), but using D-α-amino-(1,4-cyclohexadienyl)acetamidopenicillanic acid instead of D-α-aminophenylacetamidopenicillanic acid, trihydrate.

Method Bvi. As (Bi), but using ethylchloroformate instead of iso-butyl chloroformate and D-α-aminocyclopropylacetamidopenicillanic acid, trihydrate.

Method Bvii. As (Bi), but using D-α-aminovaleramidopenicillanic acid instead of D-α-aminophenylacetamidopenicillanic acid, trihydrate.

Method Bviii. As (Bi), but using ethylchloroformate instead of isobutyl chloroformate, and D-α-amino-(2-thienyl)-acetamidopenicillanic acid instead of D-α-aminophenylacetamidopenicillanic acid, trihydrate.

Method Bix. As (Bi), but using D-α-amino-β-phenylpropionamidopenicillanic acid instead of D-α-aminophenylacetamidopenicillanic acid.

(No Method C)

Method D

Amino-penicillin (5 m.moles) in dry dimethylformamide (100ml) was treated with triethylamine (12 m.moles) and stirred to give a clear solution. Sulphur trioxide-triethylamine complex (6 m.moles) was added portionwise over 5 mins. at room temperature and stirred for 1 hour. A solution of potassium 2-ethyl hexoate (ca 15 m.moles) in dry acetone (150ml) was added and a white solid separated.

After further dilution with acetone (200ml) the solid was filtered, washed with acetone and then stirred in dry ether for 20 mins. to remove any residual dimethylformamide. The solid was filtered and dried in vacuo.

METHOD E

Anhydrous D-α-aminophenylacetamidopenicillanic acid (5m. mole) in dry methylene dichloride (50 ml) was treated with triethylamine (~10 m. mole) to give a clear solution. Trimethylsilyl chloride (10 m. mole) was added and the mixture refluxed under nitrogen for 1 hour, then cooled to 0°C.

α-Guanidino-acid (5 m. mole) was dissolved in dry dimethylformamide (5 ml) and dry dimethylformamide (5 ml.) and dry methylene dichloride (50 ml) added, cooled to 0°C and stirred for 5 mins. with dicyclohexylcarbodi-imide (5.5 m. mole). The bis-trimethylsilylated penicillin was added and stirred at 0°C for 1 hour. The mixture was then cooled to −20°C and the dicyclohexylurea removed by filtration. The filtrate was evaporated to dryness in vacuo and the residue dissolved in acetone (20 ml)/water (20 ml) and the pH adjusted to 2.5 with 5N hydrochloric acid. After stirring at pH 2.5 for 25 mins. the acetone was removed in vacuo and any solid filtered off. The residual aqueous solution was freeze dried and the resultant solid treated with water at pH 2. The product was filtered and dried.

METHOD F

Dicyclohexylcarbodi-imide (5.5 m. mole) was added to a stirred solution of N-substituted-amino acid (5 m. mole) in dry acetone (20 ml) at 0°C. The mixture was stirred for 15 mins. at 0°–5°C and then left in the refrigerator overnight.

D-α-Aminophenylacetamidopenicillanic acid, trihydrate (5m. mole) was dissolved in acetone (10 ml)/water (10 ml) with triethylamine (0.7 ml) and the hydroxysuccinimide ester filtered in, through Celite. After stirring for 45 mins. the acetone was removed in vacuo, leaving a gelatinous mass. Acidification with 5N hydrochloric acid in aqueous ethyl acetate gave the product as the free acid (sometimes only after concentration of the ethyl acetate layer and treatment with ether) or as the salt by treatment of the washed and dried ethyl acetate layer with sodium or potassium 2-ethyl hexoate.

Method Fi. As F, but the hydroxysuccinimide ester formed in dry dimethylformamide (or dimethylformamide diluted with acetone).

Method Fii. As F, but the hydroxysuccinimide ester formed in dry 1,2-dimethoxyethane.

Method Fiii. As (Fi), but the penicillin dissolved in acetone/chloroform, the product coming out of solution as the amine salt.

EXAMPLE 1

D-α-[D-β-(p-Hydroxyphenyl)-α-ureidopropionamido]phenylacetamido penicillanic acid ($R = Ph$; $R^1 = -p-HO-PhCH_2$; $R^3 = H$; $R^2 = NHCONH_2$; $M = H$; $\alpha^1 = D$). Prepared by method (Bi), from D-β-(-p-Hydroxyphenyl)-α-ureidopropionic acid. Yield: 68%

$\nu$max (KBr): 3550, 1770, 1650, 1515, 1230 and 700cm$^{-1}$

δ[(CD$_3$)$_2$SO]: 1.44 (3H. s.gem methyl); 1.57 (3H. s. gem methyl); ~2.8 (2H. m. -$\underline{CH}_2$CH<); 4.29 (1H. s. C-3 proton); ~4.5 (1H. $_\alpha$m. -$\underline{CH}_2$CH<); 5.35 – 5.87 (5H. m. β-lactams, Ph C$\underline{H}$-; NHCO$\underline{NH}_2$*) 6.27 (1H. d. N$\underline{H}$CONH$_2$*);

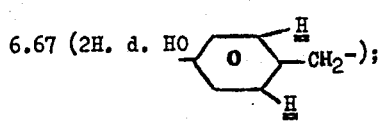
6.67 (2H. d.

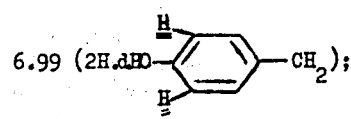
6.99 (2H.d.

7.30 (5H. broad s. Ph CH<); 8.47 (1H. m. —CONH*); 9.12 (1H. m. —CONH*—).
* Removable in D₂O.
NH₂OH Assay: 101%
Biochromatography: 1 zone at R_f 0.32

EXAMPLE 2

D-α-[D-β-(-p-Hydroxyphenyl)-α-ureidopropionamido]-(-p-hydroxyphenyl) acetamidopenicillanic acid.

(R = -p-HO-Ph; R¹ = -p-HO-PhCH₂; R³ = H; R² = NHCONH₂; M=H; α¹ =D). Prepared by method (Bi), from D-β-(-p-hydroxyphenyl)β-ureidopropionic acid and amoxycillin.

Yield: 74%

νmax (KBr); 3350 (broad), 1770, 1650, 1515, 1230 and 840 cm⁻¹.

δ[(CD₃)₂SO]: 1.42 (3H. s gem methyl); 1.57 (3H. s. gem methyl); ~2.8 (2H. m. —CH₂CH<); 4.3 (1H.s. C-3 proton); ~4.4 (1H. m. CH₂CH<); 5.3 – 5.85 (5H. m. β-lactams, Ph CH— ; NHCONH₂*); 6.25 – 7.30 (8H. m. aromatics protons); 8.47 (1H. m. CONH*—); 9.12 (1H. m. —CONH*—).
* Removable in D₂O.
NH₂OH assay: 94%
Biochromatography: 1 zone at R_f = 0.18.

EXAMPLE 3

D-α-[D-β-(p-Hydroxylphenyl)-α-ureidopropionamido] (3-thienyl)acetamido penicillanic acid.

(R =

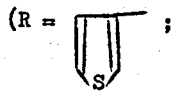

; R¹ = p—HO—PhCH₂; R³ = H; R² = NHCONH₂; M=H; α¹ =D). Prepared by method (Bii), from D-β-(p-hydroxyphenyl)-α-ureidopropionic acid and α-amino-(3-thienyl) acetamido penicillanic acid.

Yield: 72%

νmax (KBr): 3350 (broad); 1770, 1650, 1515, 1230, 845 and 780cm⁻¹.

δ[(CD₃)₂SO]: 1.45 (3H. s. gem methyl); 1.58 (3H s. gem methyl); ~2.8 (2H. m. —CH₂CH<); 4.3 (1H.s . C-3 proton), ~4.4 (1H. m. —CH₂CH<); 5.35 – 5.90 (5H. m. β-lactams, Ph —CH — ; NHCONH₂*); 6.25 (1H. m. NH CONH₂); 6.5 – 7.6 (7H. m. aromatics); 8.5 (1H. d. CONH*); 9.1 (1H. d.CONH*).
*Removable in D₂O.
NH₂OH assay: = 96%
Biochromatography: 1 zone at R_f = 0.31

EXAMPLE 4

D-α-[DL-β-(-p-Nitrophenyl)-α-ureidopropionamido]-(-p-hydroxyphenyl)acetamidopenicillanic acid.

(R = p-HO—Ph; R¹ = p-NO₂—PhCH₂; R³ = H; R² = NHCONH₂; M=H; α¹ = DL). Prepared by method (Bii), from DL-β-(-p-Nitrophenyl)-α-ureidopropionic acid and amoxycillin.

Yield: 60%

νmax (KBr): 3350, 1770, 1650, 1514 and 1230 cm⁻¹.

δ[(CD₃)₂SO]: 1.42 (3H. s. gem methyl); 1.55 (3H. s. gem methyl); 3.0 (2H. m. CH₂CH<); 4.05 (1H. s. C-3 proton); ~4.60 (1H. m —CH₂CH<); 5.25 – 5.80 (5H. m. β-lactams,

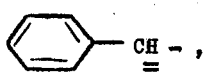

CH — ,

NHCONH₂* ); 6.2 (1H. m. NH*CONH₂); 6.5 – 8.2 (8H. m. aromatics); 8.50, 9.00 (2 x 1H.m. CONH*).
*Removable in D₂O.
NH₂OH assay: 86.5%
Biochromatography: 1 zone at R_f = 0.44

EXAMPLE 5

Sodium D-α-[DL-γ-Methylthio-α-ureidobutyramido]-phenylacetamidopenicillanate.

(R = Ph; R¹ = CH₃S (CH₂)₂—; R³ =H; R² = NHCONH₂; M=Na; α¹ =DL). Prepared by Method B, from N-Carbamoyl-DL-methionine and ampicillin, isolated as the sodium salt after treatment with sodium 2-ethylhexoate.

Yield: 51%.

νmax (KBr): 3320 (broad), 1775, 1650, 1530, 1310, 1230 and 702cm⁻¹.

δ[(CD₃)₂SO]: 1.48 (34.s. gem methyl); 1.58 (3H.s. gem methyl); 1.4 – 2.2 (2H. m. —SCH₂CH₂CH<); 2.05 (3H. d. MeS-); 2.3 – 2.7 (2H. m. SCH₂—); 4.24 (1H. s. C-3 proton); 4.1 – 4.6 (1H. m.SCH₂CH₂CH<); 5.2 – 5.9 (5H. m. β-lactams, PhCH<and -CONH₂* ); 6.4 (1H. m. CONH*—); 7.40 (5H. m. aromatics); 8.60 and 9.00 (2 x 1H. d. CONH*—).
*Removable in D₂O.
NH₂OH assay: 93.8%
Biochromatography: 1 zone at R_f = 0.36.

EXAMPLE 6

Sodium D-α-[DL-γ-Methylthio-α-ureidobutyramido](p-hydroxyphenyl)acetamido penicillanate.

(R = p—HO—Ph; R¹ = CH₃S (CH₂)₂; R³ = H; R² = NHCONH₂; M=Na; α¹ =DL). Prepared by method (Bii), from N-Carbomoyl-DL-methionine and amoxycillin, isolated as the sodium salt after treatment with sodium 2-ethylhexoate.

Yield: 43%.

νmax (KBr): 3350 (broad), 1770, 1650, 1510, 1235cm⁻¹.

δ[(CD₃)₂SO]: 1.45 (3H.s. gem methyl); 1.57 (3H.s. gem methyl); 1.4 – 2.2 (2H. m. —SCH₂CH₂CH<); 2.05 (3H. d. MeS—); 2.3 – 2.7 (2H. m. SCH₂—); 4.24 (1H.s. C-3 proton); 4.1 – 4.6 (1H. m. SCH₂CH₂CH<); 5.2 – 5.9 (5H.m.β-lactams, Ph CH< and CONH₂*); 6.4 (1H. m. CONH*—); 6.3 – 7.34 (4H. m. aromatics); 8.60 and 8.90 (2 ×1H.d.CONH*—).
*Removable in D₂O.
NH₂OH assay: 85.5%
Biochromatography: 1 zone at R_f = 0.29.

EXAMPLE 7

Sodium D-α-[DL-α-formamide-γ-methylthiobutyramido]-phenylacetamido penicillanate (R = Ph; R¹ = CH₃S (CH₂)₂; R³ = H; R² = NHCHO; M=Na; α¹ = DL). Prepared by Method B, using N-Formyl-DL-methionine and ampicillin, isolated as the sodium salt after treatment with sodium 2-ethyl hexoate.

Yield: 63%.

νmax (KBr): 3300 (broad), 1780, 1732, 1645, 1525, 1302, 1225 and 700 cm⁻¹·

δ[(CD₃)₂SO]: 1.46 (3H. s.gem methyl); 1.55 (3H. s.gem methyl); 1.7 – 2.2 (2H. m. CH₃SCH₂CH₂CH<); 2.05 (3H. d. CH₃S—); 2.3 – 2.7 (2H. m. CH₃S CH₂CH₂); 4.23 (1H. s . C-3 proton; 4.70 (1H. m. —CH NHCHO); 5.3 – 5.9 (3H. m. β-lactams and PhCH<); 7.37 (5H. m. aromatics); 8.08 (1H. s .NHCHO); 8.31, 8.60 and 9.00 (3 × 1H. d. -CONH*—).

* Removable in D₂O.

NH₂OH assay: 100%

Biochromatogram: Single zone at R_f = 0.40.

EXAMPLE 8

D-α-[DL-β-(p-Chlorophenyl)-α-ureidopropionamido]-(p-hydroxyphenyl)acetamidopenicillanic acid.

(R = p-HO-Ph; R¹ = p-Cl—PhCH₂—; R³ = H; R² = NHCONH₂; M=H; α¹ = DL). Prepared by Method (Bii) from DL-β-(P-Chlorophenyl-α-ureidopropionic acid and amoxycillin.

Yield: 45%.

νmax (KBr): 3360, 1770, 1650, 1514 and 1230 cm⁻¹

δ[(CD₃)₂SO]: 1.42 (3H. s . gem dimethyl); 1.58 (3H. s .gem dimethyl); 2.86 (2H. m. —CH₂CH<); 4.26 (1H. s . C-3 proton); 4.55 (1H. m. —CH₂CH<); 5.58 (5H. m. β-lactams, NHCONH₂*); 6.24 (1H. m. NHCONH₂*); 6.78 and 7.27 (8H. m. Cl—⟨⟩—CH₂—,

HO—⟨⟩—CH<);

8.53 (1H. m. CONH*); 9.04 (1H. m. CONH).
* Removable in D₂O.

Biochromatography: R_f = 0.42

Analysis: C₂₆H₂₈N₅O₇SCl required: C, 52.93; H, 4.75; N, 11.87; S, 5.43; Cl, 6.02. Found: C, (50.23); H, 4.79; N, 11.13; S, 5.32; Cl, 5.97.

EXAMPLE 9

D-α-[DL-β-(p-Fluorophenyl)-α-ureidopropionamido]-phenylacetamido penicillanic acid (R = Ph; R¹ = p-F-PhCH₂; R³ = H; R² = NHCONH₂; M =H; α¹=DL) Prepared by method B from DL-β-(p-fluorophenyl)-α-ureidopropionic acid and ampicillin.

Yield: 42%.

νmax (KBr): 3360, 1773, 1651, 1510, 1226 and 720 cm⁻¹.

δ[(CD₃)₂SO]: 1.42 (3H.s . gem methyl); 1.57 (3H.s .gem methyl); 1.57 (3H. s. gem methyl); 2.87 (2H. m. CH²CH<); 4.24 (1H.ˢ . C-3 proton); 4.56 (1H. m. CH₂CH<); 5.65 (5H. m. β-lactams, α-proton, —NH-CONH₂*), 6.27 (1H. d. NHCONH₂*); 7.24 (9H. m. Ph CH<);

(F—⟨⟩—CH₂);

8.62 (1H. m. —CONH—*); 9.17 (1H. m. CONH*).
* Removable in D₂O.

Biochromatography: 1 Spot at R_f = 0.42.

EXAMPLE 10

D-α-[DL-β-(p-Chlorophenyl)-α-ureidopropionamido]phenylacetamido penicillanic acid (R = Ph; R¹ = p-Cl—PhCH₂; R³ = H; R² = NHCONH₂; M=H; α¹ = DL). Prepared by Method B, from DL-β-(p-chlorophenyl)-α-ureidopropionic acid.

Yield: 38%

νmax (KBr): 3360, 1770, 1650, 1514 and 1230 cm⁻¹.

δ[(CD₃)₂SO]: 1.40 (3H.s .gem methyl); 1.56 (3H.s .gem methyl); 2.85 (2H. m. —CH₂CH<); 4.25 (1H.s . C-3 proton); 4.55 (1H. m. —CH₂CH<); 5.58 (5H. m. β-lactams,

⟨⟩—CH< (α);

NHCONH₂); 6.25 (1H. m. NHCONH₂); 7.30 (9H.m. aromatic protons) 8.53 (1H. m. CONH); 9.00 (1H. m. CONH).

NH₂OH Assay: 94%.

Biochromatography: 1 zone at R_f = 0.59.

EXAMPLE 11

Sodium D-α-[DL-β-(p-Nitrophenyl)-α-ureidopropionamido]-phenylacetamidopenicillanate.

(R = Ph; R¹ = p-NO₂—PhCH₂; R³ = H; R² = NHCONH₂; M=Na; α¹ = DL). Prepared by method B, from DL-β-(p-Nitrophenyl)-α-ureidopropionic acid and ampicillin; isolated as the sodium salt by treatment with sodium 2-ethylhexoate.

Yield: 55%

νmax (KBr); 3350, 1770, 1650, 1514 and 1230 cm⁻¹.

δ[(CD₃)₂SO]: 1.42 (3H. s. gem methyl); 1.60 (3H. s. gem methyl); 3.0 (2H. m. -CH₂CH<); 4.20 (1H.s. C-3 proton); 4.7 (1H. m. -CH₂CH<); 5.3 – 5.85 (5H.m. β-lactams,

⟨⟩—CH— (α),

NHCONH₂*); 6.2 (1H. m. NH*CONH₂); 7.18 – 8.25 (9H. m. aromatics); 8.50, 9.05 (2 × 1H. m. CONH*).
* Removable in D₂O.

NH₂OH assay: 93.9%

Biochromatography: 1 zone at R_f = 0.5.

EXAMPLE 12

D-α-(D-p-Phenyl-α-ureidopropionamido)-(p-hydroxyphenyl)acetamidopenicillanic acid (R = -p—HO—Ph; R¹ = PhCH₂; R³ = H; R² = NHCONH₂; M=H; α¹ = D). Prepared by method (Biii), using D-β-phenyl-α-ureidopropionic acid and amoxycillin.

Yield: 63% M.P. 235°–238°C.

νmax (KBr): 3360 (broad), 1740, 1650, 1520 and 1230 cm⁻¹.

δ[(CD₃)₂SO]: 1.47 (3H. s. gem methyl); 1.60 (3H. s. gem methyl); 2.95 (2H. m. Ph.CH₂.CH<); 4.27 (1H. s. C-3 proton); 4.60 (1H. m. PhCH₂CH<); 5.30 – 5.80 (5H. m. β-lactams, ureido-NH₂*,

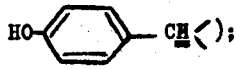

6.20 (1H. d. ureido-NH*—);

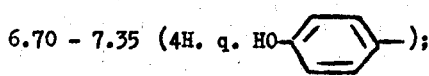

7.25 (5H.s. benzyl aromatics), 8.50 (1H. d. —CONH—*); 9.00 (1H. d. —CONH*—).
* Removable in D₂O.

Hydroxylamine Assay: 107.7%
Biochromatography: One zone at R_f = 0.35
Analysis for C₂₆H₂₉N₅O₇S; Required (%) C, 56.22; H, 5.23; N, 12.61; S, 5.77. Found (%) C, (55.33); H, 5.44; N, 11.99; S, 5.44.

EXAMPLE 13

D-α-Acetamido-β-Phenylpropionamido)-Phenyl-Acetamido-Penicillanic Acid (R = Ph: R¹ = PhCH₂; R³ = H; R² = NHCOCH₃; M = H; α¹ = DL).

Prepared by method (Bi), from DL-α-acetamido-β-phenylpropionic acid and ampicillin.

Yield: 94%

ν_max (KBr ): 33.60 (broad) 1774, 1648, 1511, 1215 and 701cm⁻¹

δ[(CH₃)₂SO]: 1.43 (3H.s. gem - methyl); 1.56 (3H.s. gem - methyl); 1.77 (3H.s. NHCOCH₃); 2.7–3.2 (2H.m. PhCH₂CH <) 4.24 (1H.s. C-3 proton); 4.6–4.9 (1H.m PhCH₂CH <); 5.62 (3H.m. β-lactams, PhCH <); 7.38 (10H.m. PhCH<; Ph CH₂CH <); 8.0–9.3 (3H.m. removable in D₂O, —CONH—)

Hydroxylamine Assay: 62.1%
Biochromatography: 1 zone at R_f = 0.26
Analysis: C₂₇H₃₀N₄O₆S required: C, 60.22; H, 5.58; N, 10.41; S, 5.95. Found: C,(57.45); H, 5.69; N, 9.98; S, 6.03.

EXAMPLE 14

D-α-[DL-α-(3-Methylureido)-β-Phenyl-Propionamido]-Phenylacetamido Penicillanic Acid ( R = Ph: R¹ = PhCH₂; R³ = NHCONHCH₃; M = H; α¹=DL).

Prepared by method (Bi), starting from DL-α- (3methylureido)-β-phenylpropionic acid and ampicillin.

Yield: 75% ν_max (KBr); 1775, 1637, 1560, 1490, 1297, 1219 and 702cm⁻¹. δ[(CD₃)₂SO]: 1.45 (3H.s. gem-methyl); 1.57 (3H.s. gem-methyl); 2.52 (3H.s. NHCONHCH₃ ); 2.90 (2H.m. PhCH₂CH<); 4.27 (1H.s. C-3 proton); 4.63 (1H.m. PhCH₂CH<); 5.64 (3H.m. β-lactams, PhCH₂<); 7.32 (10H.m. PhCH₂CH<; Ph CH<); 8.63 (1H.m. removable in D₂O,—CONH —); 9.18 (1H.m. removable in D₂O —CONH —); ca 6.25 (broad signal due to —NH CONH—).

Biochromatography: 1 zone at R_f = 0.47

Analysis: C₂₇H₃₁N₅O₆S required: C, 58.48, H, 5.60; N, 12.64; S, 5.78 Found: C, (56.78); H, 5.59; N, 12.73; S, 5.05

EXAMPLE 15

D-α-[DL-β-(-p-Fluorophenyl)-α-Ureido-Propionamido]-(-p-Hydroxyphenyl)-Acetamido-Pencillanic Acid (R = -p-HO—Ph; R¹ = —p-F—PhCH₂; R³ = H; R² = NHCONH₂; M = H, α¹ = DL)

Prepared by method (Bii), from DL-β-(-p-fluorophenyl)-α-ureidopropionic acid and amoxycillin.

Yield: 48%

ν_max (KBr): 3360, 1764, 1650, 1510, 1224, and 838cm⁻¹

δ[(CD₃)₂SO]: 1.43 (3H.s. gem-methyl); 1.54 (3H.s. gem-methyl); 2.88 (2H.m. -CH₂CH<); 4.14 (1H.s. C-3 proton); 4.2–4.8 (1H.M. CH₂CH<); 5.3-7.5 (extremely strong signals containing β-lactams,

—NHCONH₂ *,

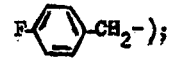

δ = 8.3–9.2 (2H.m. —CONH—*)
removable in D₂O

Hydroxylamine Assay: 84.7%
Biochromatography: 1 zone at R_f = 0.41

EXAMPLE 16

D-α-[D-β-Phenyl-α-(n-Valeramido)-Propionamido] Phenylacetamido Penicillanic Acid (R = Ph; R¹ = PhCH₂; R³ = H; R² = NHCO(CH₂)₃CH₃; M = H; α¹ = D).

Prepared by method (Bi), from N -valeroyl-D-β-phenylalanine

Yield: 19% ν_max(KBr): 3290 (br), 1772, 1635, 1525, 1300, 1224, 733, 702^(cm⁻¹). δ[(CD₃)SO]; 0.82 (3H.m. (CH₂)₃CH₃), 1.0–1.7 (4H.m. CH₂CH₂CH₂CH₃) 1.45 (3H.s. gem-methyl), 1.58 (3H.s. gem-methyl), 2.09 (2H.m. CH₂(CH₂)₂CH₃), 3.00 (2H.m. PhCH₂), 4.28 (1H.s. C-3 proton), 4.78 (1H.m. PhCH₂CH<) 5.4–5.9 (3H.m. β-lactams and PhCH<), 7.2–7.5 (10H.m. aromatic protons), 8.05 (1H.d. —CONH—), 8.47 (1H.m. CONH), 9.13 (1H.m. —CONH—).

NH₂OH Assay: 90%
Biochromatography: Single zone R_f 0.70
Analysis: Found: C, 60.96, H, 6.05; N, 9.46; S, 5.65% C₃₀H₃₈N₄O₆S requires C, 62.10; H, 6.21; N, 9.66; S, 5.52

EXAMPLE 17

D-α-[D-β-Phenyl-α-Pivaloylaminopropionamido]-Phenylacetamido Penicillanic Acid (R = Ph; R¹ = PhCH₂; R³ = H; R² = —NHCOC(CH₃)₃; M = H; α¹ = D).

Prepared by method (Bi), from α-t-Butyramido-D-β-phenyl propionic acid.

Yield: 6%

ν_max(KBr): 3350(br), 1772, 1639, 1517, 1300, 1212, 702cm⁻¹.

δ[(CD₃)₂SO]: 0.97 (9H.s. (CH₃)₃), 1.39 (3H.s. gem-methyl), 1.52 (3H.s. gem-methyl), 2.97 (2H.m.

PhCH$_2$), 4.20 (1H.s. C-3 proton), 5.35–5.85 (4H.m. β-lactams and PhCH<), 4.65 (1H.m. PhCH$_2$CH<), 7.25 (5H.s. phenyl protons), 7.39 (5H.m. phenyl protons), 7.2–7.6 (1H.m. —NHCO—*), 8.50 (1H.d. —NHCO—*), 9.27 (1H.d. —NH—CO—).
* removed by D$_2$O.
NH$_2$OH Assay: 102%
Biochromatography: 0.71

EXAMPLE 18

D-α-[D,L-α-Benzamido-β-Phenylpropionamido]-Phenylacetamido Penicillanic Acid (R = Ph; R$^1$ = PhCH$_2$; R$^3$ = H; R$^2$ = NHCOPh; M = H; α$^1$ = D,L). Prepared by method (Bi), from α-Benzamido-D,L-β-phenylpropionic acid.
Yield: 22%
$\nu_{max}$ (KBr): 3300, 1775, 1635, 1522, 1302, 122, 702cm$^{-1}$
δ[(CD$_3$)$_2$SO]: 1.42 (3H.s. gem-methyl), 1.57 (3H.s. gem-methyl) 3.11 (2H.m. PhCH$_2$), 4.24 (1H.s. C-3 proton), 5.00 (1H.m. PhCH$_2$CH<), 5.4–5.9 (3H.m. β-lactams and PhCH<), 7.2–8.0 (10H.m. aromatic protons), 8.65, 8.80 and 9.20 (3 × 1H.d. —NHCO—*).
* removed in D$_2$O.
NH$_2$OH Assay: 88%
Biochromatography: Single zone 0.70

EXAMPLE 19

D-α-[D,L-γ-Phenyl-α-Ureidobutyramido]-p-Hydroxyphenylacetamido Penicillanic Acid ( R = p HO—Ph; R$^1$ = PhCH$_2$CH$_2$—; R$^3$=H; R$^2$= —NHCONH$_2$ M = H; α$^1$ = D,L). Prepared by method (Biii), from α-ureido-D,L-α-phenylbutyric acid.
Yield: 35%
$\nu_{max}$ (KBr): 3315(br), 1770, 1650, 1510, 1454, 1227, 842, 703cm$^{-1}$
δ[(CD$_3$)$_2$SO]: 1.42 (3H.s. gem-methyl), 1.52 (3H.s. gem-methyl), 2.00 (2H.m. PHCH$_2$CH$_2$ ), 2.52 (2H.m. PhCH$_2$CH$_2$), 4.1–4.4 (1H.m. PhCH$_2$CH$_2$ CH<), 4.25 (1H.s. C-3 proton), 5.3–5.8 (3H.m. β-lactams and PhCH<), 7.25 (9H.m. aromatic protons), 6.34, 6.73 (2 × 1H.d. NHCO*), 8.32–9.10 (3H.m. —CONH—* and —CONH$_2$*)
* removed by D$_2$O
NH$_2$OH Assay: 80%
Biochromatography: R$_f$ 0.5

EXAMPLE 20

D-α-[D,L-α-Formamido-β-Phenylpropionamido]-Phenylacetamido Penicillanic Acid (R = Ph; R$^1$ = $^{PhCH}$$_2$; R$^3$ = H; R$^2$ = —NHCHO; M = H; α$^1$ = D,L). Prepared by method (Bi) from N-Formyl-D,L-phenylalanine.
Yield: 55%
$\nu_{max}$ (KBr): 3242(br), 1771,,1638, 1522, 1379, 1300, 1226, 731, 701cm$^{-1}$.
δ[(CD$_3$)$_2$SO]: 1.46 (3H.s. gem-methyl), 1.59 (3H.s. gem-methyl); 2.88 (2H.m. PhCH$_2$CH<), 4.21 (1H.s. C-3 proton), 4.83 (1H.m. PhCH$_2$CH<), 5.4–5.9 (3H.m. β-lactams and PhCH<), 7.2–7.6 (10H.m. aromatic protons), 7.97 (1H.s. CHO), 2.27, 2.70 and 9.11 (3 × 1H.d. —NHCO*—).
* removed by D$_2$O.
NH$_2$OH Assay: 79%
Biochromatography: Single zone R$_f$ 0.52

EXAMPLE 21

D-α-[D-β-Phenyl-α-Propionamido Propionamido]-Phenylacetamido Penicillanic Acid (R = Ph; R$^1$ = PhCH$_2$; R$^3$ = H; R$^2$ = NHCOCH$_2$CH$_3$; M = H; α$^1$ = D). Prepared by method (Bi) from α-Propionamido-D-β-phenylpropionic acid.
Yield: 13%
$\nu_{max}$ (KBr): 3229(br), 1770, 1637, 1524, 1226, 702cm$^{-1}$.
δ[(CD$_3$)$_2$SO]: 0.89 (3H.t. COCH$_2$CH$_3$), 1.42 (3H.s. gem-methyl), 1.60 (3H.s. gem-methyl), 1.98 (2H.m. —NHCH$_2$CH$_3$), 2.90 (2H.m. PhCH$_2$CH<), 4.21 (1H.s. C-3 proton), 4.70 (1.H.m. PhCH$_2$CH<), 5.4–5.9 (3H.m. β-lactams and PhCH <), 7.2–7.6 (10H.m. aromatic protons), 8.01, 8.42 and 9.10 (3 × 1H.d. —CONH*—).
* removed by D$_2$O.
NH$_2$OH Assay: 75%
Biochromatography: Single zone R$_f$ 0.58

EXAMPLE 22

D-α-[D-α-Isobutyramido-β-Phenylropionamido]-Phenylacetamido Penicillanic Acid (R = Ph; R$^1$ = PhCH$_2$—; R$^3$ = H; R$^2$ = NHCOCH(CH$_3$)$_2$; M = H; α$^1$ = D. Prepared by method (Bi), from α-isobutyramido-D-β-phenyl propionic acid
Yield: 18%
$\nu_{max}$ (KBr): 3300 (br,) 1771, 1638, 1526, 1300, 1222, 702cm$^{-1}$.
δ[(CD)$_2$SO]: 0.85 (6H.t. CH(CH$_3$)$_2$, 1.41 (3H.s. gem-methyl), 1.56 (3H.s. gem-methyl), 2.97 (2H.m. PhCH$_2$CH<), 4.25 (1H.s. C-3 proton), 4.70 (2H.m. CH (CH$_3$)$_2$ and PhCH$_2$CH<), 5.4–5.9 (3H.m. β-lactams and PhCH<), 7.1–7.6 (10H.m. aromatic protons), 7.97, 8.47 and 9.13 (3 × 1H.d. —NH CO—*).
* removed by D$_2$O.
NH$_2$OH Assay: 103%
Biochromatography: Single zone R$_f$ 0.66

EXAMPLE 23

D-α-[D-α-Methylthio-γ-Ureidobutyramido]-Phenylacetamido Penicillanic Acid (R = Ph; R$^1$ = CH$_3$S(CH$_2$)$_2$—; R$^3$ = H; R$^2$ = —NHCONH$_2$; M = H; α$^1$ = D). Prepared by method (Fi), from N-Carbamoyl-D-methionine.
Yield: 43%
$\nu_{max}$ (KBr): 3320(br), 1775, 1650, 1530, 1310, 1230, and 702cm$^{-1}$
δ[(CD$_3$)$_2$SO]: 1.48 (3H.s. gem-methyl), 1.61 (3H.s. gem-methyl), 1.4–2.2 (2H.m. -SCH$_2$CH$_2$CH<), 2.1 (3H.s.CH$_3$S—), 2.3–2.7 (2H.m. —SCH$_2$CH$_2$CH) 5.2–5.9 (5H.m.β-lactams, PhCh and —CONH$_2$*) 6.4 (1H.m. —CONH —*)
* removed by D$_2$O.
NH$_2$OH Assay: 98%
Biochromatography: Single zone R$_f$ 0.34
Analysis: Found: C, 49.33; H, 5.64; N, 12.94; S, 11.59%. C$_{22}$H$_{29}$N$_5$O$_6$S$_2$ requires C, 50.48; H, 5.54; N, 13.38; S, 12.24%.

EXAMPLE 24

D-α-[D,L-α-Methyl-α-Ureidovaleramido]-Phenylacetamido Penicillanic Acid (R = Ph; R$^1$ = (CH$_3$)$_2$CHCH$_2$—; R$^3$ = H; R$^2$ = —NHCONH$_2$; M = H; α$^1$=D,L)

Prepared by method B from α-methyl-D,L-α-ureido valeric acid.

Yield: 36%

$\nu_{max}$ (KBr): 3325(br), 1775, 1723, 1650, 1530, 1310, 1222, 702 cm$^{-1}$ δ[(CD$_3$)$_2$SO]: 0.84 and 0.95 (2 × 3H.s. CH(CH$_3$)$_2$), 1.45 (3H.s. gem-methyl), 1.61 (3H.s. gem-methyl), 0.78–2.0 (3H.m. CH$_2$CH(CH$_3$)$_2$), 4.25 (1H.s. C-3 proton), 4.0–4.6 (1H.m. >CHNHCONH$_2$), 5.3–5.9 (5H.m. β-lactams, PhCH< and CONH$_2$*), 6.2 (1H.d. —CONH—), 7.2–7.6 (5H.m. aromatic protons), 8.48 and 9.04 (2 × 1H.d. —CO—NH—*)

* removed by D$_2$O.

NH$_2$OH Assay: 79%

Biochromatography: Single zone R$_f$ 0.44

EXAMPLE 25

D-α[ D,L-α-Formamido-β-(p-hydroxyphenyl) propionamido]phenylacetamido penicillanic acid (R=Ph; R'=pHO—PhCH$_2$—; R$^3$ = H; R$^2$=NHCHO; M=H; α'=D,L). Prepared by method B from N-Formyl-D,L-Tyrosine.

Yield: 23%

$\nu_{max}$ (KBr): 3290 (br.), 1773, 1735, 1650, 1518, 1378, 1230 and 701 cm$^{-1}$ δ[ (CD$_3$)$_2$SO] 1.45 (3H.s gem. methyl), 1.62 (3H.s.gem.methyl), 2.7–3.2 (2H.m. PhCH$_2$—), 4.24 (1H.s C3 proton), 4.8 (1H.m. >CHNHCHO), 5.35–5.96 (3H.m βLactams and ph CH<), 6.7 and 7.0 (2 × 2H.m. pHO—C$_6$H$_4$—), 7.36 (5H.m. Aromatic protons), 7.92 (1H.s. —NHCHO), 8.2 (1H.d —CONH—*) 8.7 and 9.12 (2 × 1H.m.—CONH—*).

*removed by D$_2$O.

NH$_2$OH Assay: 105%

Biochromatogram: Single zone R$_f$0.39.

EXAMPLE 26

D-α-[D-α-Formamido-γ-methylthiobutyramido]-phenylacetamido penicillanic acid.

(R=Ph; R'=CH$_3$S (CH$_2$)$_2$—;R$^3$=H; R$^2$=—NHCHO; M=H; α'=D). Prepared by method (Fii) from N - Formyl-D-methionine.

Yield: 5.8%

$\nu_{max}$ (KBr): 3300 (br), 1780, 1732, 1645, 1525, 1302, 1225, 700 cm$^{-1}$.

δ [ (CD$_3$)$_2$SO]: 1.46 (3H.s gem. methyl), 1.55 (3H.S. gem methyl), 1.7–22 (2H.m. CH$_3$SCH$_2$CH$_2$CH<), 2.0 (s. 15–17% of L-CH$_3$ SCH$_2$CH$_2$C*H<) 2.1 (S.83–5% of D-CH$_3$SCH$_2$CH$_2$C*H<), 2.3–2.7 (2H.m. CH$_3$SCH$_2$CH$_2$CH$_2$), 4.23 (1H.S. C$_3$ proton), 4.70 (1H.m. >CHNHCHO), 5.3–5.9 (3H.m. β-lactams, and PhCH<), 7.37 (5H.m. aromatic protons), 8.08 (1H.s-NH-CHO), 8.31, 8.59 and 9.02 (3 × 1H.d.—CONH— removed by D$_2$O).

NH$_2$OH Assay: 102%

Biochromatogram: Single zone Rf 0.41

EXAMPLE 27

D - α-[D-γ-Methyl-α-ureidovaleramido]-phenylacetamido penicillanic acid.

(R=Ph; R'= (CH$_3$)$_2$ CHCH$_2$; R$^3$=H; R$^2$=NHCONH$_2$; M=H; α'=D) Prepared by method (Fi) from γ-methyl-D-α-ureido valeric acid.

Yield: 28% M.p: 168-170°C (Decomp.)

$\nu_{max}$ (KBr): 3315 (br.), 1775, 1730, 1650, 1530, 1310, 1220, 700 cm$^{-1}$.

δ[(CD$_3$)$_2$SO]: 0.85 and 0.92 (6H.d. CH(CH$_3$)$_2$), 1.50 (3H.S gem. methyl) 1.66 (3H.S gem.methyl), 0.8–2.0 (3H.m. CH$_2$CH (CH$_3$)$_2$), 4.28 (1H.s. C3 proton), 4.1–4.5 (1H.m. CH NHCONH$_2$), 5.3–5.9 (5H.m. β-lactams PhCH< and CONH*$_2$), 6.22 (1H.d.—CONH*—), 7.36 (5H.m. aromatic protons), 9.07 and 9.40 (2 × 1H.d. — CO NH*—)

* removed by D$_2$O.

NH$_2$OH Assay: 95%

Biochromatogram: Single zone Rf0.45

Analysis: Found: C,54.71; H, 6.15; N,13.78; S,6.49%. C$_{23}$H$_{31}$N$_5$O$_6$S requires C, 54.65, H, 6.14; N, 13.86; S,6.34%.

EXAMPLE 28

D-α-[L-γ-Methylthio-α-ureidobutyramido] phenylacetamido penicillanic acid (R=Ph; R'= (CH$_3$) S (CH$_2$)$_2$—; R$^2$=H; R$^2$=NHCONH$_2$; M=H, α'=L). Prepared by method (Fi) from N-Carbamoyl-L-methionine.

Yield: 19% M.p.: 163°–6°C (Decomp.)

$\nu_{max}$ (KBr): 3350 (br), 1775, 1650, 1522, 1305, 1220, 702 cm$^{-1}$.

δ[(CD$_3$)$_2$SO]: 1.46 (3H.s gem.methyl), 1.60 (3H.s.gem.methyl) 1.5–2.2 (2H.m. CH$_3$ CH$_2$ CH$_2$ CH<), 2.00 (3H.s.CH$_3$S) 2.2–2.6 (2H.m. CH$_3$ SCH$_2$CH$_2$CH), 4.27 (1H.S. C3 proton), 4.38 (1H.m. CH$_3$CH$_2$CH$_2$CH<), 5.60 (5H.m β lactams, PhCH< —CONH*$_2$), 7.39 (5H.m. aromatic protons), 6.34 (1H.m. —CHCONH*$_2$), 9.12 and 9.48 (2 × 1H.d —CONH*—)

*removed by D$_2$O

NH$_2$OH Assay: 100%

Biochromatogram: Single zone Rf0.38

Analysis: Found: C,49.64; H, 5.98; N,13.08; S,11.72%. C$_{22}$H$_{29}$N$_5$O$_6$S$_2$ requires C 50.48; H,5.54; N,13.38; S,12.24%

EXAMPLE 29

Triethylammonium D-α-[D-β-(3-Indolyl)-α-ureidopropionamido]phenylacetamido penicillanate (R=Ph;

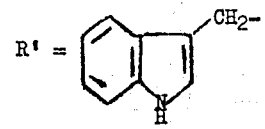

R$^3$=H; R$^2$=NHCONH$_2$; M=HN (CH$_2$CH$_3$)$_3$; α'=D. Prepared by method (Fiii) from N - Carbamoyl-D-Tryptophan Yield: 52% M.p.: 200°–3°C (Decomp).

$\nu_{max}$ (KBr): 3350 (br), 1767, 1660, 1640, 1610, 1530, 1458, 1392, 749 cm$^{-1}$.

δ[(CH$_3$)$_2$SO]: 1.11 (3H.t.OCH$_2$CH$_3$), 1.42 (3H.s. gem. methyl), 1.53 (3H. s.gem methyl), 2.7–3.2 (4H.m.-CH$_2$CH< and OCH$_2$CH$_3$), 4.00 (1H.s. C$_3$ proton), 4.59 (1H.m. CH$_2$CH<) 5.3–5.9 (5H.m. β lactams, RhCH< and CONH*$_2$), 6.9–7.7 (10H.m. aromatic protons), 6.29, 8.53 and 8.97 (3 × 1H.d. —NHCO*), 10.84 (1H.s. indolyl NH* ).

*removed by D$_2$O.

NH$_2$OH Assay: 94%

Biochromatogram: Single zone Rf0.30

Analysis: Found: C,59.38; H,6.65; N, 14.35; S,4.60% C$_{34}$H$_{45}$N$_7$O$_6$S requires C,60.07; H,6.67; N,14.42, S,4.72%

EXAMPLE 30

Triethylammonium
D-α-[D,L-α-formamido-β-(3-indolyl)-propionamido]-phenylacetamido penicillinate (R= Ph:

$R^3$=H; $R^2$=—NHCHO;M=HN $(CH_2CH_3)_3$; α'=D,L. Prepared by method (Fi) from N - Formyl-D,L-tryptophan, the product crystallising on dilution with ether.

Yield: 50%

$\nu_{max}$ (KBr): 3310 (br), 1772, 1770, 1665, 1530, 1458, 1388, 1218, 748 cm$^{-1}$.

δ[(CD$_3$) SO]: 1.17 (3H.t.OCH$_2$CH$_3$), 1.44 (3H.s. gem.methyl), 1.58 (3H.s. gem methyl), 2.8-3.3 (4H.m. OCH$_2$ CH$_3$ and CH$_2$CH<), 4.12 (1H.s. C$_3$ proton), 4.90 (1H.m. CH$_2$ CH<), 5.3 – 5.9 (3H.m. β-lactams and Ph CH<), 7.0-7.8 (11H.m. 10 aromatic protons and NHCONH$_2$) 8.00 (1H.S. CHO), 8.0–9.0 (4H.m. 2 X-NHCO* and —CONH$_2$*), 10.80 (1H.s indolyl NH*)
*removed by D$_2$O.

NH$_2$OH Assay: 183%

Biochromatogram: Single zone Rf0.36.

EXAMPLE 31

Triethylammonium -α-[D-γ-carbamoyl-α-Ureido butyrylamido] phenylacetamido penicillanate (R=Ph; R'=H$_2$NCO $(CH_2)_2$—; $R^3$=H; $R^2$=—NHCONH$_2$; M=HN $(CH_2CH_3)_3$; α'=D. Prepared by method (Fi) from N-carbamoyl-D-glutamine, the product crystallising on dilution with ether.

Yield: 77%

$\nu_{max}$ (KBr): 3400 (br.), 1773, 1698, 1660, 1603, 1532, 1458, 1397, 1314, 1220, 703 cm$^{-1}$.

δ[(CD$_3$)$_2$SO]: 1.16 (3H.t.OCH$_2$CH$_3$), 1.43 (3H.s. gem. methyl), 1.54 (3H.s. gem methyl), 1.5-2.2 (4H.m. — CH$_2$CH$_2$—), 4.1(1H.s.C3proton), 4.88 (1H.m. CH Ch$_2$CH$_2$), 5.3-5.8 (3H.m β-lactams and PhCH<), 6.3 (1H.m.—NHCO*—), 7.3-7.7 (6H.m. aromatic protons and —NHCO*—), 8.2-9.0 (5H.m. 2 × —CONH*$_2$) and —CONH*
*removed by D$_2$O NH$_2$OH Assay: 100%

Biochromatogram: Single zone Rf0.34

EXAMPLE 32

D-α-[D,L-β-Phenyl-α-ureidopropionamido]-1,4-cyclohexadienylacetamidopenicillanic acid.

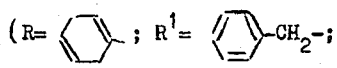

$R^3$=H; $R^2$=—NHCONH$_2$: M=H; α'=D,L). Prepared by method (Bv) from D,L-β-phenyl-α-ureidopropionic acid.

Yield: 65%

$\nu_{max}$(KBr): 3340, 1762, 1720, 1650, 1530, 1230 and 703cm$^{-1}$

δ [(CD$_3$)$_2$SO]: 1.5(6H.d. gem-dimethyls); 2.6(4H.s. cyclohexadiene methylenes); 2.6-3.2(2H.m. PhCH$_2$CH<); ); 4.3(1H.s.C-3proton); 4.3-4.8(1H.m. PhCH$_2$CH<); 4.9-5.9 (5H.m.β-lactams,

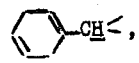

—NHCONH$_2$*);5.67(3H.s. cyclohexadiene methines);6.3–6.7(1H.m. -NHCONH$_2$*);7.25(5H.s.PhCH$_2$CH<);8.0–8.3(1H.m.—CONH—*);8.6–9.0(1H.m.—CONH—*);
*Removable with D$_2$O Hydroxylamine Assay: 59%.
Biochromatography: Rf 0.56.

EXAMPLE 33

Sodium
D-β-[D-β-Phenyl-β-ureidopropionamido]-1,4-cyclohexadienylacetamido penicillanate

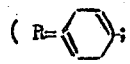

$R^1$=PhCH$_2$ ; $R^3$=H; $R^2$=—NHCONH$_2$; M=Na; α'=D) Prepared by method (Bvi) from D-β-phenyl-α-ureidopropionic acid and epicillin.

Yield: 45%.

$\nu_{max}$(KBr): 3350, 1760, 1630, 1530, 1230 and 703cm$^{-1}$

δ[(CD$_3$)$_2$SO]: 1.53(6H.d.gem-dimethyls); 2.65(4H.s.cyclohexadienyl methylenes); 2.8–3.0(2H.m.PhCH$_2$—);4.0(1H.s.C-3 proton); 4.2-4.7(1H.m.)CH$_2$CH—);5.0–5.6(5H.m.β-lactam protons HNCHCO and HNCONH$_2$):5.7(3H.s. cyclohexadienyl vinylic protons); 6.4–6.7(1H.m. –NHCONH$_2$); 7.25(5H.s.Ph); 8.0–9.0(2H.m.NH)

Hydroxylamine Assay: 76%.
Biochromatography: 1 zoneat Rf 0.47

EXAMPLE 34

D-α-[DL-β-Benzyloxy-α-ureidopropionamido]-phenylacetamidopenicillanic acid.

( R=Ph; $R^1$=PhCH$_2$OCH$_2$; $R^3$=H; $R^2$=NHCONH$_2$; M=H; α'=DL). Prepared by method (Bi) from β-benzyloxy-α-ureido-DL-propionic acid and ampicillin.

Yield: 56%.

$\nu_{max}$ (KBr): 3350, 1770, 1650, 1520, 1220 and 700cm$^{-1}$

δ[(CD$_3$)$_2$SO]: 1.5(6H.d gem dimethyls); 3.65(2H.m. —OCH$_2$CHC<) 4.25(1H.s.C-3 proton); 4.5(3H.m. —OCH$_2$CH<and PhCH$_2$O—); 5.4–7.0(6H.m. β-lactam protons, HN—CHCO and —NHCONH$_2$); 7.2–7.5(10H.m. 2xphenyl aromatics); 8.5-9.2(2H.m. amide NH's)

Analysis: C$_{22}$H$_{31}$N$_5$O$_7$S.H$_2$O required: C,55.3; H,5.63: N,11.9. Found: C,56.03;H,5,72: N,11.46.

Hydroxylamine Assay: 95%.
Biochromatography: 1 zone at Rf 0.42.

EXAMPLE 35

D-α-[DL-β-Benzyloxy-α-ureidopropionamido]-p-hydroxyphenylacetamido penicillanic acid.

(R= p-HO—Ph; $R^1$=PhCH$_2$OCH$_2$; $R^3$=H; $R^2$=—NHCONH$_2$; M=H; α'=DL). Prepared by method (Biii) from DL-β-benzyloxy-α-ureidopropionic acid and amoxycillin.

Yield: 59%.

$\nu_{max}$ (KBr): 3350, 1775, 1725, 1650, 1515, 1230, and 703 cm$^{-1}$

δ[(CD$_3$)$_2$SO]: 1.5(6H.d. gem dimethyls); 3.5–3.9(2H.m. —OCH$_2$CH<); 4.23 (1H.s. C-3 proton); 4.3–4.7(3H.m. PhCH$_2$O and OCH$_2$CH<); 5.2–5.9(5H.m. β-lactams, HNCHCO and CONH$_2$) 6.2–6.5 (1H.m. -NHCONH$_2$); 6.5–7.5(9H.m. aromatic protons) 8.3–9.0 (2H.m. amide NH's)
Hydroxylamine Assay: 84%.
Biochromatography: 1 zone at Rf 0.3

EXAMPLE 36

D-α-[D-β-Phenyl-α-ureidopropionamido]-3-thienyl acetamido penicillanic acid

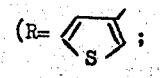

R$^1$=PHCH$_2$-; R$^3$=H; R$^2$=-NHCONH$_2$; M=H, α$^1$=D). Prepared by method (Biv) from D-β-phenyl -α-ureido-propionic acid.
Yield: 59%. M.p. 175°–7°C (decomp.)
ν$_{max}$ (KBr): 3360, 1750, 1650, 1525 and 704 cm$^{-1}$
δ[(CD$_3$)$_2$SO]: 1.53(6H.m. gem dimethyls); 2.92(2H.m. PhCH$_2$CH<) 4.28(1H.s. C-3proton); 4.61(1H.m. PhCH$_2$CH<); 5.31-6.05 (5H.m. β-lactams, CONH$_2$* and ThCH <); 6.26(1H.d. CONH—*); 7.37(8H.m. Ph and Th);8.58 and 9.07 (2×1H.d. —CONH—*)
* removed by D$_2$O
Hydroxylamine Assay: 100%.
Biochromatogram : 1 zone at Rf 0.40

EXAMPLE 37

D-β-[D-α-Ureidopropionamido]-phenylacetamido penicillanic acid.

( R=Ph; R$^1$=CH$_3$; R$^3$=H; R$^2$=NHCONH$_2$; M=H; α$^1$=D). Prepared by method (Bi) from D-α-ureidopropionic acid.
Yield: 28%. M.p. 176°–8°C (decomp.)
ν$_{max}$(KBr): 3350 (br), 1773, 1720, 1635, 1530, 1234, and 700 cm$^{-1}$
δ [(CD$_3$)$_2$SO]: 1.21 (3H.d. CH$_3$CHNH—); 1.43 (3H.s. gem dimethyls); 1.57 (3H.s. gem dimethyls); 4.26 (1H.s. C-3 proton); 4.33(1H.m. CH$_3$CHNH—); 5.35–5.91(5H.m. β-lactams, PhCH< and CONH$_2$*); 5.91–6.54 (1H.m. —NHCONH$_2$); 7.38(5H.m. aromatic protons); 8.47 and 9.05 (2x1H.d. —CONH—*)
*removed by D$_2$O
Hydroxylamine Assay: 106%.
Biochromatogram: 1 zone at Rf 0.21

EXAMPLE 38

D-α-[D,L-β-PHENYL-α-UREIDO-PROPIONAMIDO]-PHENYLACETAMIDO PENICILLANIC ACID (R = Ph ; R$^1$ = PhCH$_2$ R$^3$ = H ; M = H ; α$^1$ = D,L).
Prepared by method B from D,L-β-Phenyl-α-ureido propionic acid.
Yield: 37%
ν$_{max}$ (KBr): 3350 (br.), 1775, 1650, 1525, 1225, 702cm$^{-1}$.
δ[(CD$_3$)$_2$SO]: 1.45 (3H.s. gem methyl), 1.57 (3H.s. gem methyl), 2.88 (2H.m. PhCH$_2$—), 4.26 (1H.s. C3proton), 4.60 (1H.m. PhCH$_2$CH<), 5.33- 5.94(5H.m. β-lactams, PhCH,—CONH$_2$*), 6.24 (1H.d.—CONH*—), 7.27 (10H.m. aromatic protons), 8.54 (1H.d.—CONH*—), 9.11 (1H.d.—CONH*—)

*removed by D$_2$O
NH$_2$OH Assay: 87%
Biochromatogram: Single zone R$_f$0.42.

EXAMPLE 39

D-α-[-α-Methyl-α-Ureidopropionamido]-Phenylacetamido Penicillanic Acid (R = Ph ; R$^1$ = R$^3$ = CH$_3$—; R$^2$ = NH$_2$CONH— ; M = H). Prepared by method B from α-Ureido-isobutyric acid
Yield: 6%
ν$_{max}$ (KBr): 3400 (br.), 1785, 1715, 1650, 1535, 1225 and 700Cm$^{-1}$
δ[(CD$_3$)$_2$SO]: 1.38 (6H.s. (CH$_3$)$_2$C<), 1.46 (3H.s. gem methyl) 1.57 (3H.s. gem methyl), 4.27 (1H.s. C3 proton), 5.37–5.88 (5H.m. β-lactams, CONH$_2$*, Ph CH<), 6.37 (1H.s. —NHCO*—), 7.40 (5H.m. aromatic protons), 8.13 and 9.08 (2 × 1H.d.—CONH*—)
removed by D$_2$O
NH$_2$OH Assay: —
Biochromatogram: Single zone R$_f$0.27
Analysis: Found; C,52.60; H,5.89; N,14.34; S,6.88%
C$_{21}$H$_{27}$N$_5$O$_6$S required C,52.82; H,5.70; N,14.67; S,6.71%

EXAMPLE 40

D-α-[D,L-α-Methyl-β-Phenyl-α-Ureidopropionamido]-Phenylacetamido Penicillanic Acid (R = Ph; R$^1$ = $^{PhCH}$$_2$—; R$^3$ = CH$_3$, R$^2$ = NHCONH$_2$, α' = D,L)
Prepared by method B from D,L-α-Methyl-β-phenyl-α-ureidopropionic acid.
Yield: 43%
ν$_{max}$ (KBr): 3370 (br.), 1775, 1720, 1655, 1525, 1220 and 704 cm$^{-1}$.
δ[(CD$_3$)$_2$SO]:

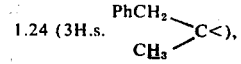

1.43 (3H.s. gem. methyl), 1.57 (3H.s. gem methyl), 2.80-3.70(2H.m.PhCH$_2$—), 4.30 (1H.m. C3 proton), 5.38–6.12 (5H.m. β-lactams, PhCH and CONH$_2$ * ), 6.23 (1H.s.—CONH—), 7.39 (10H.m. aromatic protons), 8.34(1H.d.—CONH—*), 9.28(1H.d.-CONH—*) * removed by D$_2$O
Biochromatogram: Single zone R$_f$ 0.54.
Analysis: Found; C56.49; H,5.66; N,12.16%. C$_{27}$H$_{31}$N$_5$O$_6$S requires C,58.58; H,5.64; N,12.65%

EXAMPLE 41

D-α-[D,L-α-Acetamido-βPhenylpropionamido]-p-Hydroxyphenylacetamido PENICILLANIC ACID (R = p HO-Ph; R$^1$ = PhCH$_2$; R$^3$ = H ; R$^2$ = —NHCOCH$_3$ ; M = H; α$^1$ = D,L).
Prepared by method (Bii) from N-Acetyl-D,L-β-phenylalanine.
YIELD: 40%
ν$_{max}$ (Nujol): 3250 (br.), 1760, 1630, 1515, 1380, 1220, 710cm$^{-1}$.
δ[(CD$_3$)$_2$SO]: 1.43 (3H.s. gem methyl), 1.57 (3H.s. gem methyl) 1.75 (3H.s. —NHCOCH$_3$), 3.0 (2H.m. PhCH$_2$), 4.24 (1H.s. C3 proton), 6.72 (1H.m. PhCH$_2$CH<), 5.4-5.9 (3H.m. β-lactams and PhCH<), 6.58–7.50 (9H.m. aromatic protons), 8.10, 8.47 and 8.95 (3 × 1H.m. —CONH—*).

removed by D₂O.
NH₂OH Assay: 105%
Biochromatogram; Single zone R_f 0.51

EXAMPLE 42

D-α-[L-β-(p-Methoxyphenyl)-α-Ureidopropionamide]Phenylacetamido Penicillanic Acid (R = Ph ; R₁ = pMeO—PhCH₂— ; R³ = H; R² = —NHCONH₂ ; M = H; α¹ = L).

Prepared by method B from α Ureido-L-β-(p Methoxyphenyl) propionic acid.
Yield: 19%
$\nu_{max}$ (KBr): 3300 (br.), 1775, 1640, 1515, 1250 and 700cm⁻¹.
δ[(CD₃)₂SO]: 1.45 (3H.s. gem methyl), 1.58 (3H.s. gem methyl), 2.83 (2H.m. PhCH₂), 3.72(3H.s. CH₃O), 4.28 (1H.s. C3 proton), 4.61 (1H.m. PhCh₂CH), 5.35–5.93 (5H.m. β-lactams, PhCH, —NHCONH₂*), 6.27 (1H.d. —NHCO—), 6.67–7.50 (9H.m. aromatic protons), 8.70 and 9.32 (2 × 1H.d. —NHCO—*)
Removed by D₂O
NH₂OH Assay: 81%
Biochromatogram: Single zone R_f 0.43.

EXAMPLE 43

D-α-[D-α-Guanidino-β-Phenylpropionamido]-Phenylacetamido Penicillanic Acid Hydrochloride (R = Ph ; R¹ =PhCH₂—;

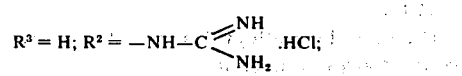

M = H α¹ = D).

Prepared by method E from D-α-Guanidino-β-phenyl propionic acid.
Yield: 21%
$\nu_{max}$ (KBr): 3330 (br.), 1768, 1663, 1602, 1525, 1458 1394, 1320, 703cm⁻¹.
δ[(CD₃)₂SO]: 1.44 (3H.s. gem methyl), 1.57 (3H.s. gem methyl), 2.96-3.23 (2H.m. PhCH₂—), 4.17(1H.m. C3 proton), 4.61 (1H.m. PhCH₂CH<), 5.30-5.94 (3H.m. β-lactams and PhCH<), 7.11–7.71 (14H.m. aromatic protons and

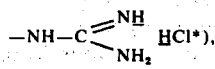

8.14–8.47

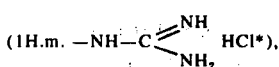

8.82 and 9.12 (2 × 1H.m. —CONH—*)
* removed by D₂O
NH₂OH Assay: 90%
Biochromatogram: Single zone R_f 0.52

EXAMPLE 44

D-α-[D,L-β-Methoxy-α-Ureidopropionamido]-Phenyl-Acetamido Penicillanic Acid (R = Ph ; R¹ = CH₃OCH₂ ; R³ = H ; R² = —NHCONH₂ ; M = H ; α = D,L).

Prepared by method B from D-α-Ureido-β-methoxy propionic acid.
Yield: 23%
$\nu_{max}$ (KBr): 3350 (br.), 1775, 1650, 1520, 1310, 1225, 1115 and 700cm⁻¹.

δ[(CD₃)₂SO]: 1.45 (3H.s. gem methyl), 1.58 (3H.s. gem methyl), 3.27 (3H.d. CH₃OCH₂—), 3.57 (2H.m. CH₃OCH₂—), 4.18–4.75 (1H.m. —CH₂CH<), 4.27 (1H.s. C3proton), 5.23–5.98(5H.m. β-lactams, —NH-CONH₂*, PhCH<), ), 6.37 (1H.d.—NHCO—*), 7.38 (5H.m. aromatic protons) 8.42 (1H.d. —CONH—*), 9.14 (1H.m.—CONH—*).
* Removed by D₂O
NH₂OH Assay: 98%
Biochromatogram: Single zone R_f = 0.24

EXAMPLE 45

PHTHALID-3-yl D-α-[D-α-GUANIDINO-β-PHENYLPROPIONAMIDO] PHENYLACETAMIDO PENICLLINATE, HYDROCHLORIDE (R = Ph; R¹ = PhCH₂- ; R³= H ;

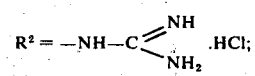

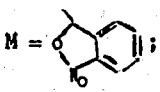

α¹ = D).

Prepared by method A from D-α-Guanidino-β-phenyl propionic acid.
Yield: 23%
νmax (KBr): 3340 (br.), 1785, 1660, 1510, 1285, 980 755 and 705cm⁻¹.
δ[(CD₃)₂SO]: 1.53 (6H.m. gemdimethyls), 3.03 (2.H.m. PhCH₂CH), 4.56 (1H.s. C3 proton), 4.37-5.08 (1H.m. PhCH₂CHC), 5.33–6.01 (3H.m. β-lactams and PhCH), 7.52 (1H.s. Phthalide 3 proton), 6.95–8.05 (19H.m. aromatic protons and

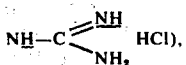

8.05–9.49 (2 × 1H.m. —CONH—*)
* Removed by D₂O
NH₂OH Assay: 91%
Biochromatogram; Single zone R_f 0.87

EXAMPLE 46

D-α-[L-β-Phenyl-α-Ureidopropionamido]-Phenylacetamido Penicillanic Acid (R = Ph ; R¹ = PhCH₂ ; R³ = H ; R² = —NHCONH₂ ; M = H ; α¹ = L).

Prepared by method (Bi) from D-α-Ureido-β-phenyl propionic acid.
Yield: 15%
$\nu_{max}$ (KBr): 3360 (Br.), 1775, 1650, 1525, 1315, 1230 and 705cm⁻¹.
δ[(CD₃)₂SO]: 1.44 (3H.s. gem methyl), 1.59 (3H.s. gem methyl), 2.89 (2H.m. PhCH₂—), 4.25 (1H.s. C3 proton), 4.68 (1H.m. PhCH₂CH), 5.64 (5H.m. β-lactams NHCONH₂*, PhCH), 6.27 (1H.d. —NHCO—), 7.28 (10H.m. aromatic protons), 8.62 and 9.17 (2 × 1H.d. —CONH—*)
* Removed by D₂O.
Biochromatogram: Single zone

EXAMPLE 47

D-α-[D,L-α-(3-ETHYLUREIDO)-β-PHENYLPROPIONAMIDO]-PHENYLACETAMIDOPENICILLANIC ACID

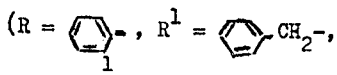

$R^3 = H$, $R^2 = NHCONHCH_2CH_3$, $M = H$, $\alpha^1 = D,L$).

Prepared by method (Bi) from D,L-(3-ethylureido)β-phenylpropionic acid.

Yield: 16% m.p. 174-6°C (dec.)

$\nu_{max}$(KBr): 3380 (broad), 1774, 1637, 1540, 1299, 1218 and 701cm$^{-1}$.

δ[(CD$_3$)$_2$SO]; 0.96 (3H.t.—NHCH$_2$CH$_2$), 1.44 (3H.s. gem methyl), 1.58 (3H.s. gem methyl), 2.96 (4H.m. PhCH$_2$CH<, —NHCH$_2$CH$_3$), 4.27 (1H.s. C3 proton), 4.59 (1H.m. PhCH$_2$CH<), 5.38-6.17 (5H.m. β-lactams, PhCH<, —NHCONH—*), 7.32 (10H.m. PhCH<, PhCH$_2$CH<), 8.58 (1H.m. —CONH—*), 9.12 (1H.m.—CONH—*).

* Removable with D$_2$O.

Hydroxylaminl Assay: 92.9%

Biochromatography: R$_f$ = 0.71

EXAMPLE 48

D-α-[D,L-β-(2-THIENYL)-α-UREIDOPROPIONAMIDO]PHENYLACETAMIDOPENICILLANIC ACID

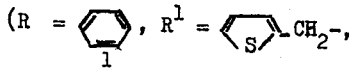

$R^3 = H—$, $R^2 = —NHCONH_2$, $M = H$, $\alpha^1 = D,L$).

Prepared by method (Bi) from D,L-β-(2-thienyl)α-ureidopropionic acid.

Yield: 25.9%

$\nu_{max}$(KBr): 3355 (br.), 1773, 1648, 1537, 1307, 1226 and 701cm$^{-1}$.

δ[(CD$_3$)$_2$SO]: 1.42 (3H.s. gem methyl), 1.56 (3H.s. gem methyl), 3.10 (2H.m. —CH$_2$CH<), 4.21 (1H.s. C3proton), 4.50 (1H.m. -CH$_2$CH<), 5.58 (5H.m. β-lactams, -NHCONH$_2$*, PhCH<), 6.28 (1H.m. —NHCONH$_2$*), 6.89 (2H.m. thienyl 3- and 4- protons), 7.35 (6H.s. phenyl aromatics and thienyl 5- proton), 8.67 (1H.m. —CONH—*), 9.15 (1H.m. —CONH—*).

* Removable with D$_2$O

Hydroxylamine Assay: 70.6%

Biochromatography: R$_f$ = 0.41

EXAMPLE 49

POTASSIUM D-α-[D-α-(3-ETHYLUREIDO)-p-PHENYL-PROPIONAMIDO]-PHENYLACETAMIDOPENICILIANATE (R = Ph—, $R^1$ = PhCH$_2$—, $R^3$ = H—, $R^2$ = —NHCONHCH$_2$CH$_3$, N = K, $\alpha^1$=D).

Prepared by method (Bi) from D-α-(3-ethylureido)-β-phenylpropionic acid.

Yield: 65.3%

$\nu_{max}$(KBr): 3350(br), 1774, 1630, 1540, 1225, 732 and 702cm$^{-1}$.

δ [(CD$_3$)$_2$SO]: 0.95 (3H.t.J = 7Hz —NHCH$_2$CH$_3$), 1.45 (3H.s. gem-methyl), 1.58 (3H.s. gem-methyl), 2.75-3.35 (4H.m. PhCH$_2$CH, —NHCH$_2$CH$_3$ (J = 7Hz)), 4.28 (1H.s. C-3 proton), 4.61 (1H.m. PhCH$_2$CH<), 5.4-6.3 (5H.m. β-lactams, PhCH: —NHCONH—*); 7.37 (10H.m. PhCH . PhCH$_2$CH<), 8.53 (1H.d. —CONH—*), 9.12 (1H.m. —CONH—*),

* removable in D$_2$O

Hydroxylamine Assay: 85.4%

Biochromatography: R$_f$ = 0.65

EXAMPLE 50

D-α-[D-β-PHENYL-α-(3-n-PROPYLUREIDO)-PROPIONAMIDO]PHENYLACETAMIDOPENICILLANIC ACID

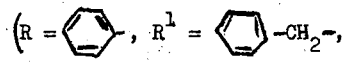

$R^3 = H$, $R^2 = NHCONHCH_2CH_2CH_3$, $M = H$, $\alpha^1 = D$)

Prepared by method (Bi) from D-α-(3-n-propylureido)-propionic acid.

Yield: 70.3%

$\nu_{max}$(KBr); 3320 (br.), 1772, 1633, 1540, 1222, 731 and 701cm$^{-1}$.

δ[(CD$_3$)$_2$SO]: 0.81 (3H.t. —NHCH$_2$CH$_2$CH$_3$), 1.45 (3H.s. gem methyl), 1.58 (3H.s. gem methyl), 2.7-3.3 (6H.m. PhCH$_2$CH<, —NHCH$_2$CH$_2$CH$_3$), 4.27 (1H.s. C-3 proton), 4.6 (1H.m. PhCH$_2$CH<), 5.4-6.3 (5H.m. β-lactams, PhCH<, —NHCONH—*), 7.31 (10H.m. PhCH<, PhCH$_2$CH<), 8.53 (1H.m. —CONH—*), 9.10 (1H.m. —CONH—*).

* Removable with D$_2$O

Hydroxylamine Assay: 94.7%

Biochromatography; R$_f$ = 0.73

EXAMPLE 51

D-α-[D-β-PHENYL-α-(3-ISO-PROPYLUREIDO)-PROPIONAMIDO]-PHENYLACETAMIDOPENICILLANIC ACID

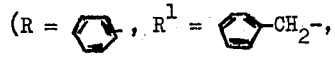

$R^3 = H—$, $R^2 = —NHCONHCH(CH_3)_2$ $M = H$, $\alpha^1 = D$).

Prepared by method (Bi) from D-α-phenyl-α-(3-isopropylureido)-propionic acid.

Yield: 60%

$\nu_{max}$ (KBr); 3363 (br), 1772, 1626, 1533, 1230, 1128, 729 and 701 cm$^{-1}$.

δ[(CD$_3$)$_2$SO]: 0.99 (6H.d. NHCH(CH$_3$)$_2$), 1.45 (3H.s. gem methyl), 1.58 (3H.s. gem methyl), 2.92 (2H.m. PhCH$_2$CH<), 3.3. (1H.m. —NHCH(CH$_3$)$_2$), 4.28 (1H.s. C-3 proton), 4.6 (1H.m. PhCH$_2$CH<), 5.4-6.3 (5H.m. β-lactams, PhCH<, —NHCONH—*), 7.23 (5H.s. PhCH$_2$CH<), 7.39 (5H.m. PhCH<), 8.4-9.5 (2H.m. 2 × —CONH—*).

* Removable with D$_2$O

Hydroxylamine Assay: 89.7%

Biochromatography: R$_f$ = 0.72

EXAMPLE 52

POTASSIUM D-α-[D-α-(3-CYCLOHEXYLUREIDO)-β-PHENYL-PROPIONAMIDO]-PHENYLACETAMIDOPENICILLANATE

R = 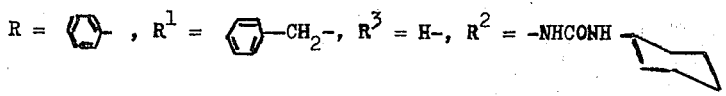, R¹ = ⌬—CH₂—, R³ = H—, R² = —NHCONH—⌬

M = K, α¹ = D.

Prepared by method (Bi) from D-α-(3-cyclohexylureido)-β-phenylpropionic acid.

Yield: 57%

$\nu_{max}$ (KBr): 3330 (br.), 1762, 1628, 1546, 1392, 1320 and 701cm⁻¹.

δ[(CD₃)₂SO]: 0.6-1.7 (10H.m. cyclohexyl methylenes) 1.44 (3H.s gem methyl), 1.54 (3H.s. gem methyl), 2.75 – 3.4 (3H.m. PhCH₂CH<, -NH-CH), 3.92 (1H.d. C-3 proton), 4.3–4.7 (1H.m. PhCH₂CH<), 5.2–5.6 (2H.m. β-lactams), 5.65-5.94 (1H.m. PhCH<), 6.1–6.5 (2H.m. —NHCONH—*), 7.23 (5H.s. PhCH₂CH<), 7.37 (5H.m. PhCH<), 8.4–9.0 (2H.m. 2 x —CONH—*)
* Removable with D₂O Hydroxylamine Assay: 85.9%
Biochromatography: R_f = 0.73

EXAMPLE 53

Potassium D-α-[DLα-(3-tert-butylureido)-β-phenylpropionamido] phenylacetamidopenicillanate (R=Ph; R¹=PhCH₂—; R³=H; R²=—NHCONHC(CH₃)₃; M=K; α¹=D,L). Prepared by method (Bi) from D,L-α-(3-tert-butylureido)-β-phenylpropionic acid.

Yield: 40.2%.

$\nu_{max}$ (KBr): 3360(br), 1774, 1645(br), 1540(br), 1456, 1214, 733 and 702 cm⁻¹

δ[(CD₃)₂SO]: 1.22 (9H.s. -NHC(CH₃)₃); 1.45(3H.s. gem dimethyl); 1.58(3H.s. gem dimethyl); 2.89(2H.m. PhCH₂CH<) 4.23(1H.s. C-3 proton); 4.53(1H.m. PhCH₂CH<) 5.35-6.15(5H.m. β-lactams, PhCH < and —NHCONH—*); 7.30 (10H.m.PhCH < and PhCH₂CH <); 8.51(1H.d. —CONH—*); 9.12(1H d. —CONH—*).
* removable in D₂O.

Hydroxylamine Assay: 99.8%.
Biochromatography: 1 zone at Rf 0.72

EXAMPLE 54

D-β-[DL-β-(p-Hydroxyphenyl)-α-ureidopropionamido] phenylacetamidopenicillanic acid R=Ph; R¹=p-HO—PhCH₂; R³=H; R²—NHCONH₂; M=H; α¹=D,L. Prepared by method B from D,L-β-(p-hydroxyphenyl)-α-ureidopropionic acid.

Yield: 80%.

$\nu_{max}$ (KBr): 3350(br), 1772, 1650, 1517, 1230, and 703 cm⁻¹

δ[(CD₃)₂SO]: 1.44(3H.s. gem methyl); 1.57 (3H.s. gem methyl) ~2.8 (2H.m. —CH₂CH<); 4.29 (1H.s. C-3 proton) ~4.5 (1H.m -CH₂CH<); 5.35–5.87 (5H.m. β-lactams, PhCH< and >NHCONH₂*); 6.27 (1H.d. -NHCONH₂*); 6.67 (2H.d. o-protons in p-HO-Ph ring); 6.99 (2H.d. m-protons in p-HO—Ph ring); 7.30(5H. broad s. PhCH ); 8.47 (1H.m. —CONH—*) 9.12 (1H.m. —CONH—*)
* removable with D₂O.

Hydroxylamine Assay: 79.4%.
Biochromatography: 1Zone at Rf 0.27.

EXAMPLE 55

D-α-[D,L,β-(m-Hydroxyphenyl)-α-ureidopropionamido]-phenylacetamido penicillanic acid.

( R=Ph, R¹ = m-HO—PhCH₂—, R³=H, R² = —NHCONH₂, M=H, α¹=D,L ). Prepared by method B from D,L-β-(m-hydroxyphenyl)-α-ureidopropionic acid.

Yield: 46%.

$\nu_{max}$ (KBr): 3360(br), 1775, 1625, 1531, 1236, 1164, and 703 cm⁻¹

δ[(CD₃)₂SO]: 1.45 (3H.s. gem methyl); 1.58 (3H.s. gem methyl);~2.8 (2H.m. —CH₂CH<); 4.32 (1H.s. C-3 proton) 4.55 (1H.m. —CH₂CH<); 5.40-5.90 (5H.m. β-lactams, PhCH< and —NHCONH₂*); 6.35 (1H.d. —NHCONH₂*) 6.55-7.15 (4H.m. m-HO—Ph— aromatics); 7.32 (5H. broad s. PhCH<); 8.52 (1H. d. —CONH—*); 9.16 (1H.m. —CONH—*)
*removable with D₂O.

Hydroxylamine Assay: 93.7%.
Biochromatography: 1Zone at Rf 0.39

EXAMPLE 56

D-α-[D-β-Phenyl-α-ureidopropionamido]-(2-thienyl)-acetamidopenicillanic acid.

( R= 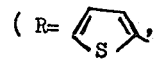,

R¹=PhCH₂—, R³=H, R²= —NHCONH₂, M=H, α¹=D). Prepared by method (Bviii) with D-β-phenyl-α-ureidopropionic acid.

Yield: 44.8%.

$\nu_{max}$ (Nujol); 3310(br), 1785, 1668, 1539, 1233 and 701 cm⁻¹

δ[(CD₃)₂SO]: 1.47(3H.s. gem methyl); 1.60(3H.s. gem methyl;~3(2H.m. PhCH₂CH<); 3.9-4.4(1H.s. PhCH₂CH<) 4.26(1H.s. C-3 proton); 5.3-6.6 (6H.m. β-lactams, ThCH<, and -NHCONH₂*); 7.28(8H. m. PhCH₂CH<and ThCH<); 7.7-9.5 (2H.m. 2x —CONH—*)
* removable with D₂O.

Hydroxylamine Assay: 78.2%.
Biochromatography: One zone at Rf 0.62 (plus faint zone at Rf 0.27 due to starting amino penicillin.)

EXAMPLE 57

D-α-[D-β-Phenyl-α-ureidopropionamido]-valeramidopenicillanic acid.

( R= CH₃(CH₂)₂—, R¹= PhCH₂—, R³=H, R²=)NHCONH₂, M=H, α¹=D). Prepared by method (Bvii) from D-β-phenyl-α-ureidopropionic acid.

Yield: 30%. $\nu_{max}$ (KBr): 3340(br), 1774, 1650, 1530, 1231, and 703cm⁻¹

δ[(CD₃)₂SO]: 0.92 (3H.m.CH₃(CH₂)₂—); 1.1–1.7 (10H. m. gemdimethyls, CH₃(CH₂)₂—); 2.85-3.0 (2H.m. PhCH₂CH<); 4.3–4.7 (2H.m. CH₃(CH₂)₂CH<, PhCH₂CH<); 4.34 (1H.s. C-3 proton); 5.47-5.8 (4H.m. β-lactams, —NHCONH₂*); 6.30 (1H.d. —NHCONH₂*); 7.27 (5H.s. aromatics); 8.12 (1H.d. —CONH—*); 8.81 (1H.m. —CONH—*)
* removable with D₂O.

Hydroxylamine Assay: 78%.
Biochromatography: 1 zone at Rf 0.59.

EXAMPLE 58

D-α-[D-β)Phenyl-α-ureidopropionamido]-cyclopropylacetamidopenicillanic acid.

( R= 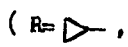 ,

R¹=PhCH₂-, R³=H, R²= -NHCONH₂, M=H, α¹=D), Prepared by method (Bvi) from D-β-phenyl-α-ureidopropionic acid.
Yield: 50%.
$\nu_{max}$ (KBr): 3345(br), 1772, 1645,(br), 1527, 1230 and 703 cm⁻¹
δ[(CD₃)₂SO]: 0.25-1.25H.m.cyclopropyl ring protons) 1.51 (3H.s. gem methyl); 1.63 (3H.s. gem methyl); 2.92 (2H.m. PhCH₂—);

4.05 (1H.m. 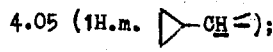 );

4.3 (1H.s. PhCH₂CH<) 5.5-5.8 (4H.m. β-lactams and —CONH₂*); 6.18 (1H.d. —CONH—*) 7.2–7.4 (5H.m. aromatic protons); 8.18 and 8.93 (2x1H.d. —CONH—*)
* removed by D₂O.

Hydroxylamine Assay: 95.6%.
Biochromatography: 1 zone at Rf 0.37

EXAMPLE 59

D-α-[D-β-PHENYL-α-UREIDOPROPIONAMIDO]-β-PHENYLPROPIONAMIDOPENICILLANIC ACID (R = R¹ = PhCH₂-, R³ = H, R² = -NHCONH₂, M=H, α¹ = D).

Prepared by method (Bix) from D-p-phenyl-α-ureidopropionic acid.
Yield: 40%
$\nu_{max}$ (KBr): 3322(br), 1725, 1638, 1534, 1302, 1231, 702cm⁻¹
δ[(CD)₃SO]: 1.51 (3H.s. gem-methyl), 1.65 (3H.s. gem-methyl), 3.0 (4H.m. PhCH₂, PhCH₂), 4.32 (1H.s. C-3 proton), 4.4 and 4.8 (2 × 1H.m. PhCH₂CH< ), 5.52 (2H.m. β-lactams), 6.1 (1H.m. —CONH—), 7.1–7.4 (10H.m. aromatic protons), 8.20 and 8.78 (2 × 1H.m. —CONH*—)
* removed by D₂O.

NH₂OH Assay: 87%
Biochromatography: Single zone Rf 0.40

EXAMPLE 60

D-α-[D-α-UREIDO-n-HEPTANAMIDO]-PHENYLACETAMIDO PENICILLANIC ACID (R = Ph; R¹ = CH₃(CH₂)₅; R³ = H; R² = -NHCONH₂; M = H; α¹ = D).

Prepared by method (Bi), from D-Ureidoheptanoic acid.
Yield: 45%
$\nu_{max}$(KB ): 3380(br), 1763, 1650, 1600, 1538, 1401, 1323, 1234, 699cm⁻¹.
δ[(CD₃)₂SO]: 0.87 (3H.m. CH₃(CH₂)₅), 1.0–2.0 (10H.m. CH₃(CH₂)₅), 1.47 (3H.s. gem-methyl), 1.56 (3H.s. gem-methyl), 3.97 (1.H.s. C-3 proton), 3.4–3.8 (1H.m. (CH₂)₅CH<), 5.3-5.9 (5H.m. β-lactams, PhCH<, —CONH₂*), 7.2-7.6 (5H.m. aromaticprotons), 6.6, 8.7 and 8.9 (3 × 1H.m. —CONH*—)
* removed by D₂O NH₂OH Assay: 37%
Biochromatography: Single zone Rf 0.67

EXAMPLE 61

D-α-[D-α-UREIDO-n-HEXANAMIDO]-PHENYLACETAMIDO PENICILLANIC ACID (R = Ph, R¹ = CH₃(CH₂)₃, R³ = H, R² = -NHCONH₂, M = H, α¹ = D.)

Prepared by method Bi) using D-α-ureidohexanoic acid.
Yield: 60%
$\nu_{max}$ (KBν): 3340, 1772, 1640, 1312, 1234, 700cm⁻¹.
δ[(CD₃)₂SO]: 0.84 (3H.m. CH₃(CH₂)₃, 1.0–1.8 (6H.m. CH₃(CH₂)₃, 1.42 (3H.s. gem-methyl), 1.54 (3H.s. gem-methyl), 4.23 (1H.s. C-3 proton), 4.23 (1H.m. CH₃(CH₂)₃CH<), 5.4-5.9 (5H.M. β-lactams, Ph.CH<and CONH₂*), 6.25 (1H.m. —CONH*—), 7.40 (5H.m. aromatic protons), 8.49 and 9.08 (2 × 1H.d. —CONH* —)
* removed by D₂O.

Hydroxylamine Assay: 73%
Biochromatography: Rf = 0.59

EXAMPLE 62

D-α-[D-β-(1,4-Cyclohexadienyl)-α-Ureidopropionamido]-(p-Hydroxyphenyl)Acetamidopenicillanic Acid (R =p—HO—Ph), R¹ = 

R³ = H, R² = —NHCONH₂, M = H, α¹ = D)
Prepared by method (Bii) using D-β-(1,4-cyclohexadienyl)-α-ureidopropionic acid
Yield: 50%
$\nu_{max}$(KBν): 3330(br), 1770, 1640, 1510, 1223, 961, and 840cm⁻¹.
δ[(CD₃)₂SO]: 1.45 (3H.s. gem-methyl); 1.58 (3H.s. gem-methyl);

2.1-2.4 (2H.m. 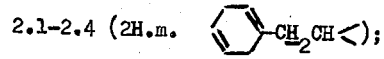 );

2.61 (4H. broad s. cyclohexadiene methylenes)); 4.24 (1H.s. C-3 proton);

4.2-4.5 (1H.m.  )

5.35-5.8 (8H.m. β-lactams,

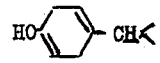

cyclohexadiene methines, —NHCONH₂*); 5.9-6.2 (1H.m. —NHCONH₂*);

6.72 (2H.d. 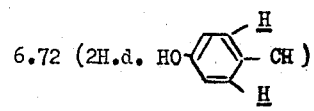 )

7.23 (2H.d. 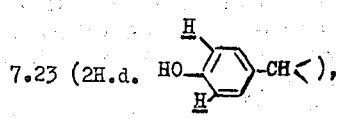

8.3 (1H.m. —CON$\underline{H}$—*); 8.9 (1H.m. —CON$\underline{H}$—*).
* removable with D₂O Hydroxylamine Assay: 98.2%

Biochromatography: R$_f$ =0.41

EXAMPLE 63

D-α-[D-β-(1,4-Cyclohexadienyl)-α-(3-Ethylureido)-Propionamido]-(p-Hydroxyphenyl)-Acetamido-Penicillanic Acid (R = HO-◯- , R¹ = ◯-CH₂-,

R³ = H—, R² = —NHCONHCH₂CH₃, M = H, α¹ = D).

Prepared by method (Bii) from D-β-(1,4-cyclohexadienyl)-α-(3-ethylureido)-propionic acid.

Yield: 20%

$\nu_{max}$ (KBr): 3350 (br), 1760, 1510, 1371, 1258, 1220 and 781cm⁻¹.

δ[(CD₃)₂SO]: 1.1-1.7 (9H.m. gem dimethyls, —NHCH₂C$\underline{H}_3$)

1.9-2.2 (2H.m. 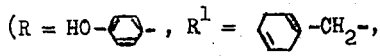

2.45-2.75 (4H.m. cyclohexadiene methylenes), 3.9-4.5(44.m. NHC$\underline{H}_2$CH₃, C-3 proton and ◯-CH₂C$\underline{H}$◯, 5.0-5.8 (8H.m. β-lactams,

HO-◯-CH◯, cyclohexadiene methines, —N$\underline{H}$*CON$\underline{H}$—*), 6.6-7.6 (4H.m. aromatics), 8.3-9.2 (2H.m. 2 x —CON$\underline{H}$—*).
* Removable in D₂O Hydroxylamine Assay: 88%

Biochromatography: R$_f$ = 0.44 (plus 2 minor zones)

EXAMPLE 64

D-α-[D-α-Acetamido-n-Hexanamido]-(p-Hydroxyphenyl)-Acetamidopenicillanic Acid (R = HO-◯),

R¹ = CH₃(CH₂)₃—, R³ = H—, R² = —NHCOCH₃, M = H, α¹ = D).

Prepared by method (Bii) from D-α-acetamido-n-hexanoic acid.

Yield: 30%

$\nu_{max}$ (KBr): 3310(br.), 1770, 1645, 1510, 1374, 1210, 1173cm⁻¹.

δ[(CD₃)₂SO]: 0.8-1.8 (9H.m. C$\underline{H}_3$(CH₂)₃—), 1.43 (3H.s. gem methyl), 1.54 (3H.s. gem methyl), 1.92 (3H.d. COC$\underline{H}_3$) 4.28 (1H.s. C3 proton), 4.38 (1H.m. CH₂C$\underline{H}$<), 5.4-5.8 (3H.m. β-lactams and PhC$\underline{h}$<), 6.22 (1H.d. —CON$\underline{H}$—*), 7.0-7.6(4H.m. aromatic protons), 8.25 and 9.3 (2 × 1H.m. —CON$\underline{H}$—*)
* Removed by D₂O Hydroxylamine Assay: 124.6%

Biochromatography: R$_f$ = 0.35 (plus small zone due to amino-penicillin).

We claim:

1. A penicillin of formula (I):

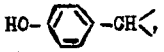

wherein

R is phenyl, hydroxyphenyl, halophenyl, nitrophenyl, alkoxyphenyl having 1-3 carbon atoms in the alkoxy part, aminophenyl, 2- or 3-thienyl, cycloalkyl having 3-7 carbon atoms in the cyclo part, cycloalkenyl having 5-7 carbon atoms in the cyclo part, or alkyl having 1-4 carbon atoms;

R¹ is acetoxy;

R² is

in which R⁵ is amino, mono- or di-alkylamino having 1-4 carbon atoms in the alkyl part, cyclohexylamino, hydrogen, alkyl of 1-4 carbon atoms or phenyl, and R⁶ is amino, mono- or di-alkylamino having 1-4 carbon atoms in the alkyl part or cyclohexylamino;

R³ is hydrogen or alkyl of 1-3 carbon atoms; or a pharmaceutically acceptable salt or a pharmaceutically acceptable hydrolyzable ester which converts to the free acid form in vivo.

2. A penicillin of claim 1 wherein the carbon atom attached to R is in the D-configuration.

3. A penicillin of claim 1 wherein the carbon atom attached to R² is in the D-configuration.

4. A penicillin of claim 1 wherein R is phenyl, 4-hydroxyphenyl or 3-thienyl.

5. A penicillin of claim 1 wherein R³ is hydrogen.

6. A penicillin of claim 1 wherein, when R² is (II), R⁵ is amino or hydrogen or, when R² is (III), R⁶ is amino.

7. A penicillin of claim 1 wherein the ester is phthalidyl, 5,6-dimethoxyphthalidyl, pivaloyloxymethyl or acetoxymethyl.

8. A penicillin of claim 1 wherein the salt is a base addition or acid addition salt.

* * * * *